United States Patent
Meng

(10) Patent No.: US 8,563,972 B2
(45) Date of Patent: Oct. 22, 2013

(54) ELECTROACTIVE MATERIALS

(71) Applicant: E I du Pont de Nemours and Company, Wilmington, DE (US)

(72) Inventor: Hong Meng, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/897,573

(22) Filed: May 20, 2013

(65) Prior Publication Data

US 2013/0248838 A1    Sep. 26, 2013

Related U.S. Application Data

(62) Division of application No. 13/599,614, filed on Aug. 30, 2012, which is a division of application No. 13/476,499, filed on May 22, 2012, which is a division of application No. 12/333,834, filed on Dec. 12, 2008, now Pat. No. 8,212,239.

(60) Provisional application No. 61/013,519, filed on Dec. 13, 2007.

(51) Int. Cl.
| | |
|---|---|
| C07D 493/04 | (2006.01) |
| C07D 495/04 | (2006.01) |
| C09K 11/06 | (2006.01) |
| C08F 34/02 | (2006.01) |
| H01L 51/54 | (2006.01) |

(52) U.S. Cl.
USPC .......................... 257/40; 526/268; 549/457

(58) Field of Classification Search
None
See application file for complete search history.

(56) References Cited

U.S. PATENT DOCUMENTS

| | | | |
|---|---|---|---|
| 6,913,710 | B2 | 7/2005 | Farrand et al. |
| 7,372,071 | B2 | 5/2008 | Li et al. |
| 7,524,922 | B2 | 4/2009 | Heeney et al. |
| 7,557,370 | B2 | 7/2009 | Li et al. |
| 7,820,782 | B2 | 10/2010 | Ong et al. |
| 7,956,199 | B2 | 6/2011 | Wigglesworth et al. |
| 8,115,200 | B2 | 2/2012 | Meng et al. |
| 2003/0209692 | A1 | 11/2003 | Farrand et al. |
| 2004/0102577 | A1 | 5/2004 | Hsu et al. |
| 2004/0127637 | A1 | 7/2004 | Hsu et al. |
| 2004/0178414 | A1 | 9/2004 | Frey et al. |
| 2005/0082525 | A1 | 4/2005 | Heeney et al. |
| 2005/0184287 | A1 | 8/2005 | Herron et al. |
| 2005/0187364 | A1 | 8/2005 | Herron et al. |
| 2005/0205860 | A1 | 9/2005 | Hsu et al. |
| 2005/0258398 | A1 | 11/2005 | Kobayashi et al. |
| 2007/0235722 | A1 | 10/2007 | Li et al. |
| 2009/0256139 | A1 | 10/2009 | Wu et al. |
| 2009/0314997 | A1 | 12/2009 | Heeney et al. |
| 2011/0028644 | A1 | 2/2011 | Brown et al. |

FOREIGN PATENT DOCUMENTS

| | | |
|---|---|---|
| JP | 10340786 A | 12/1998 |
| JP | 2005154371 A | 6/2005 |
| JP | 2007067263 A | 3/2007 |
| WO | 2004005389 A1 | 1/2004 |
| WO | 2005052027 A1 | 6/2005 |

OTHER PUBLICATIONS

Das et al., "Platinum-Catalyzed Chemoselectively Hydrative Dimerization of 2-Alkynyl-1-acetylbenzenes for One-Pot Facile Synthesis of Chrysene Derivatives," Journal of Organic Chemistry, 2007, vol. 72, pp. 9214-9218.

Frederiksen et al., "Two-Photon Photosensitized Production of Singlet Oxygen in Water," Journal of the American Chemical Society, 2005, vol. 127, pp. 255-269.

Frederiksen et al., "Two-Photon Photosensitized Production of Singlet Oxygen," Journal of the American Chemical Society, 2001, vol. 123, pp. 1215-1221.

Gustafsson et al., "Flexible Light-Emitting Diodes Made from Soluble Conducting Polymers," Nature, 1992, vol. 357, pp. 477.

Jorgensen et al., "Easy Access to 3,8-Diaryldifurano[2,3-a:2',3'-f]napthalenes. A New Extended Aromatic System," Journal of Organic Chemistry, 2000, vol. 65, pp. 8783-8785.

Kudo et al., "Angular Polycyclic Thiophenes Containing Two Thiophene Rings," Journal of Heterocyclic Chemistry 1984, vol. 21(1), pp. 185-192.

Poulsen et al., "Two-Photon Singlet Oxygen Sensitizers: Quantifying, Modeling, and Optimizing the Two-Photon Absorption Cross Section," Journal of Physical Chemistry, 2001 vol. 105, pp. 11488-11495.

(Continued)

*Primary Examiner* — Sun Jae Loewe

(57) ABSTRACT

There is provided an electroactive material having Formula I

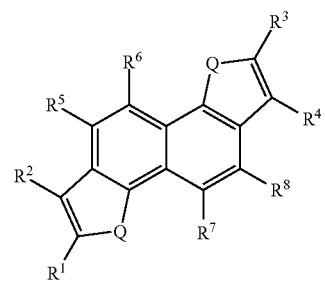

Formula I wherein:

Q is the same or different at each occurrence and can be O, S, Se, Te, NR, SO, $SO_2$, or $SiR_3$;

R is the same or different at each occurrence and can be hydrogen, alkyl, aryl, alkenyl, or alkynyl;

$R^1$ through $R^8$ are the same or different and can be hydrogen, alkyl, aryl, halogen, hydroxyl, aryloxy, alkoxy, alkenyl, alkynyl, amino, alkylthio, phosphino, silyl, —COR, —COOR, —$PO_3R_2$, —$OPO_3R_2$, or CN.

9 Claims, 1 Drawing Sheet

(56) References Cited

OTHER PUBLICATIONS

Tsuji, H. et al., "Synthesis and Properties of 2,3,6,7-Tetraarylbenzo[1,2-b:4,5-b']difurans as Hole-Transporting Material," Journal of the American Chemical Society, 2007, vol. 129, pp. 11902-11903 and Supporting Information S1-S10.

Wang, "Photoconductive Materials," Kirk-Othmer Encyclopedia of Chemical Technology, Fourth Edition, 1996, vol. 18, pp. 837-860.

Yamamoto et al., "Electrically conducting and thermally stable pi-conjugated poly(arylene)s prepared by organometallic process," Progress in Polymer Science, 1992, vol. 17, pp. 1153-1205.

Samsoniya et al., "Synthesis and Biological Activity of Some Gramine-Type Mannich Bases and their Salts," Soobshcheniya Akademii Nauk Gruzinkoi SSR, 1980, vol. 100 (2), pp. 337-340 [Abstract Only].

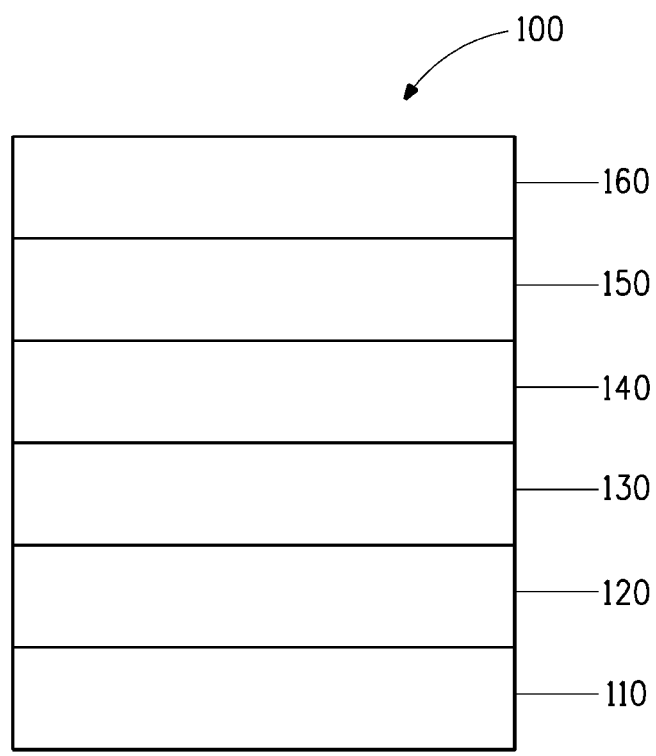

ELECTROACTIVE MATERIALS

RELATED APPLICATION

This application claims priority under 35 U.S.C. §120 from application Ser. No. 13/599,614, filed Aug. 30, 2012, (now issued as U.S. Pat. No. 8,471,251 on Jun. 25, 2013), which in turn claims priority under 35 U.S.C. §120 from application Ser. No. 13/476,499, filed May 21, 2012 (now U.S. Pat. No. 8,324,619 having issued on Dec. 4, 2012), which in turn claims priority under 35 U.S.C. §120 from application Ser. No. 12/333,834, filed Dec. 12, 2008 (now U.S. Pat. No. 8,212,239, issued on Jul. 3, 2012), which in turn claims priority under 35 U.S.C. §119(e) from Provisional Application No. 61/013,519 filed on Dec. 13, 2007, which is incorporated by reference in its entirety.

BACKGROUND INFORMATION

1. Field of the Disclosure

This disclosure relates in general to electroactive materials, their synthesis, and their use in electronic devices.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers. Additional electroactive layers may be present between the light-emitting layer and the electrical contact layer(s).

It is well known to use organic electroluminescent compounds as the active component in light-emitting diodes. Simple organic molecules, such as anthracene, thiadiazole derivatives, and coumarin derivatives are known to show electroluminescence. In some cases these small molecule materials are present as a dopant in a host material to improve processing and/or electronic properties.

There is a continuing need for new electroactive materials for electronic devices.

SUMMARY

There is provided an electroactive material having Formula I:

Formula I wherein:

Q is the same or different at each occurrence and is independently selected from the group consisting of O, S, SO, $SO_2$, Se, Te, NR, BR, PR, PO, $PO_2$, and $SiR_2$;

R is the same or different at each occurrence and is independently selected from the group consisting of hydrogen, alkyl, aryl, alkenyl, and alkynyl;

$R^1$ through $R^8$ are the same or different and are independently selected from the group consisting of hydrogen, alkyl, aryl, halogen, hydroxyl, aryloxy, alkoxy, alkenyl, alkynyl, amino, alkylthio, phosphino, silyl, —COR, —COOR, —$PO_3R_2$, —$OPO_3R_2$, and CN.

There is also provided a polymer comprising at least one repeating unit having Formula I, wherein R1 and R3 represent points of attachment to the polymer backbone.

There is also provided an organic electronic device comprising a first electrical contact, a second electrical contact and at least one electroactive layer therebetween, the electroactive layer comprising the above electroactive material.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

FIG. 1 includes an illustration of one example of an organic light-emitting diode.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Electroactive Materials, Electroactive Polymers, Devices, and finally Examples.

1. Definitions and Clarification of Terms

Before addressing details of embodiments described below, some terms are defined or clarified.

The term "alkenyl" is intended to mean a group derived from an aliphatic hydrocarbon having at least one carbon-carbon double bond. The term is intended to include heteroalkyl groups.

The term "alkoxy" is intended to mean a group having the formula —OR, which is attached via the oxygen, where R is an alkyl.

The term "alkyl" is intended to mean a group derived from a saturated aliphatic hydrocarbon and includes a linear, a branched, or a cyclic group. In some embodiments, an alkyl has from 1-20 carbon atoms. The term is intended to include heteroalkyl groups. In some embodiments, the heteroalkyl groups have from 1-20 carbon atoms and from 1-5 heteroatoms.

The term "alkylthio" is intended to mean a group having the formula —SR, which is attached via the sulfur, where R is an alkyl.

The term "alkynyl" is intended to mean a group derived from an aliphatic hydrocarbon having at least one carbon-carbon triple bond.

The term "blue luminescent material" is intended to mean a material capable of emitting radiation that has an emission maximum at a wavelength in a range of approximately 400-500 nm. "Deep blue" is intended to refer to 450-490 nm.

The term "charge transport," when referring to a layer, material, member, or structure is intended to mean such layer, material, member, or structure facilitates migration of such charge through the thickness of such layer, material, member, or structure with relative efficiency and small loss of charge. Although light-emitting materials may also have some charge transport properties, the term "charge transport layer, material, member, or structure" is not intended to include a layer, material, member, or structure whose primary function is light emission.

The term "electroactive" as it refers to a layer or a material, is intended to indicate a layer or material which electronically facilitates the operation of the device. Examples of active materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The terms "emitter" and "luminescent material" are intended to mean a material that emits light when activated by an applied voltage (such as in a light-emitting diode or light-emitting electrochemical cell).

The prefix "hetero" indicates that one or more carbon atoms has been replaced with a different atom. In some embodiments, the heteroatom is O, N, S, or a combination thereof.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The term "monomeric unit" is intended to mean a repeating unit in a polymer.

The term "organic electronic device" or sometimes just "electronic device" is intended to mean a device including one or more organic semiconductor layers or materials.

The term "phosphino" is intended to mean the group $R_2P—$, attached via the phosphorus and where R is alkyl or aryl.

The term "polymer" is intended to mean a material having at least one repeating monomeric unit. The term includes homopolymers having only one kind of monomeric unit, and copolymers having two or more different monomeric units. Copolymers are a subset of polymers. In one embodiment, a polymer has at least 5 repeating units.

The term "silyl" is intended to mean the group $R_3Si—$, attached via the silicon and where R is alkyl.

Unless otherwise indicated, all groups can be substituted or unsubstituted.

An optionally substituted group, such as, but not limited to, alkyl or aryl, may be substituted with one or more substituents which may be the same or different. Suitable substituents include alkyl, aryl, nitro, cyano, halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, thioalkoxy, $—S(O)_2—N(R')(R")$, $—C(=O)—N(R')(R")$, $(R')(R")N$-alkyl, $(R')(R")N$-alkoxyalkyl, $(R')(R")N$-alkylaryloxyalkyl, $—S(O)_s$-aryl (where s=0-2) or $—S(O)_s$-heteroaryl (where s=0-2).

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81st Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Electroactive Materials

The new electroactive materials described herein have Formula I:

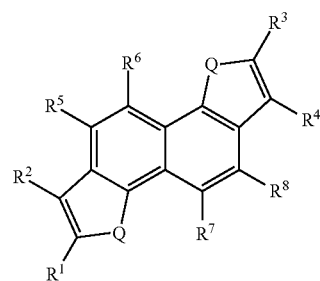

Formula I wherein:
Q is the same or different at each occurrence and is independently selected from the group consisting of O, S, SO, $SO_2$, Se, Te, NR, BR, PR, PO, $PO_2$, and $SiR_2$;

R is the same or different at each occurrence and is independently selected from the group consisting of hydrogen, alkyl, aryl, alkenyl, and alkynyl;

$R^1$ through $R^8$ are the same or different and are independently selected from the group consisting of hydrogen, alkyl, aryl, halogen, hydroxyl, aryloxy, alkoxy, alkenyl, alkynyl, amino, alkylthio, phosphino, silyl, —COR, —COOR, —PO$_3$R$_2$, —OPO$_3$R$_2$, and CN.

In some embodiments, Q is O or S. In some embodiments, Q is O.

In some embodiments, at least one of $R^1$ and $R^3$ is not hydrogen. In some embodiments, at least one of $R^1$ and $R^3$ is selected from the group consisting of alkyl, aryl, and diarylamino. In some embodiments, $R^1$ and $R^3$ are the same.

In some embodiments, at least one of $R^2$ and $R^4$ is not hydrogen. In some embodiments, at least one of $R^2$ and $R^4$ is selected from the group consisting of alkyl, aryl, and diarylamino. In some embodiments, $R^2$ and $R^4$ are the same.

In some embodiments, at least one of $R^5$, $R^6$, $R^7$, and $R^8$ is not hydrogen. In some embodiments, at least one of $R^5$, $R^6$, $R^7$, and $R^8$ is selected from the group consisting of alkyl, aryl, and diarylamino. In some embodiments, $R^5$ and $R^8$ are the same. In some embodiments, $R^6$ and $R^7$ are the same.

In some embodiments, alkyl substituents are selected from the group consisting of C1-10 linear alkyls, C1-10 branched alkyls, C2-10 linear fluoroalkyls, and C2-10 branched fluoroalkyls.

In some embodiments, aryl substituents are selected from the group consisting of Ar1 through Ar92 in Table 1 below, where the wavy line indicates the point of attachment:

TABLE 1

| Aryl substituents | |
|---|---|
| Ar | Chemical Structure of substituent |
| Ar1 | |
| Ar2 | |
| Ar3 | |
| Ar4 | |
| Ar5 | |
| Ar6 | |
| Ar7 | |
| Ar8 | |
| Ar9 | |
| Ar10 | |
| Ar11 | |
| Ar12 | |

TABLE 1-continued

Aryl substituents

| Ar | Chemical Structure of substituent |
|---|---|
| Ar13 | |
| Ar14 | |
| Ar15 | |
| Ar16 | |
| Ar17 | |
| Ar18 | |
| Ar19 | |
| Ar20 | |
| Ar21 | |
| Ar22 | |
| Ar23 | |
| Ar24 | |
| Ar25 | |
| Ar26 | |

TABLE 1-continued
Aryl substituents
| Ar | Chemical Structure of substituent |
|---|---|
| Ar27 | 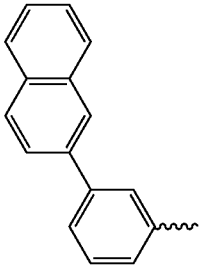 |
| Ar28 | 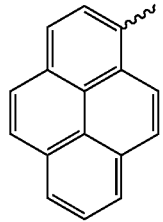 |
| Ar29 | 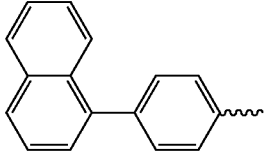 |
| Ar30 | 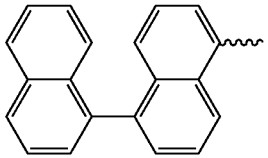 |
| Ar31 | 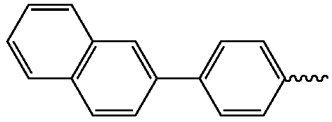 |
| Ar32 | 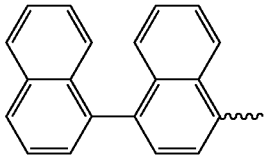 |
| Ar33 | 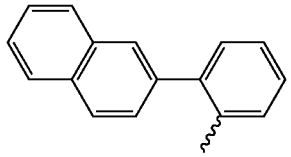 |
| Ar34 | 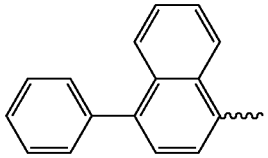 |
| Ar35 | 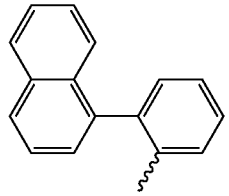 |
| Ar36 | 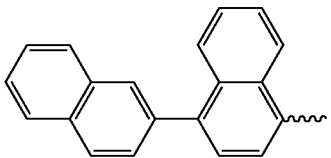 |
| Ar37 | 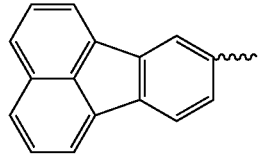 |
| Ar38 | 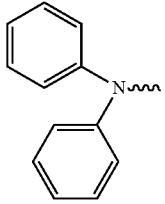 |
| Ar39 | 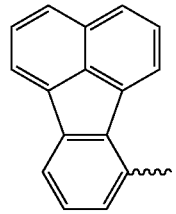 |
| Ar40 | 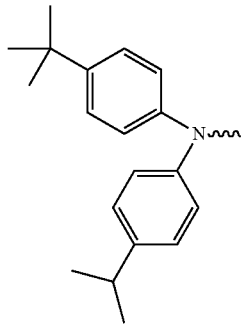 |

TABLE 1-continued
Aryl substituents
| Ar | Chemical Structure of substituent |
|---|---|
| Ar41 | 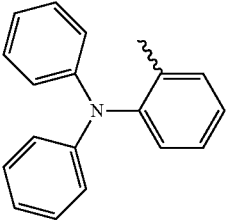 |
| Ar42 | 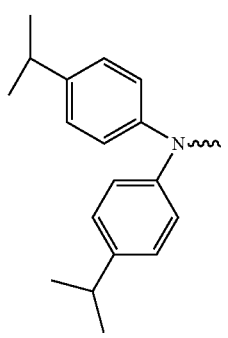 |
| Ar43 | 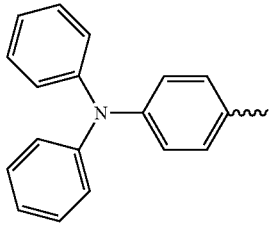 |
| Ar44 | 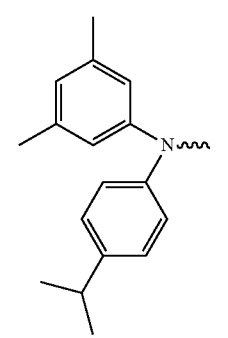 |
| Ar45 | 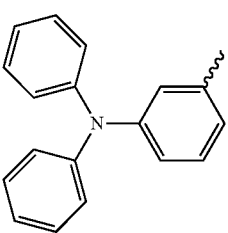 |
| Ar46 | 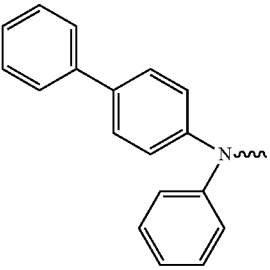 |
| Ar47 | 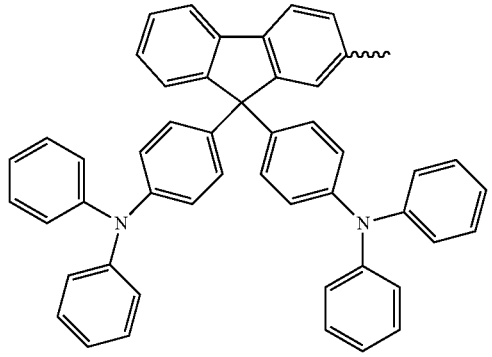 |
| Ar48 | 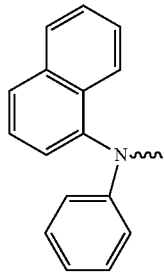 |
| Ar49 | 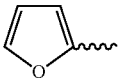 |
| Ar50 | 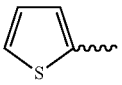 |
| Ar51 | 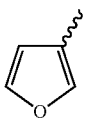 |
| Ar52 | 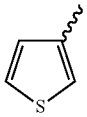 |
| Ar53 | 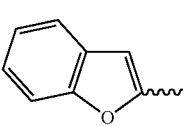 |

TABLE 1-continued
Aryl substituents
| Ar | Chemical Structure of substituent |
|---|---|
| Ar54 | 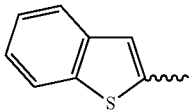 |
| Ar55 | 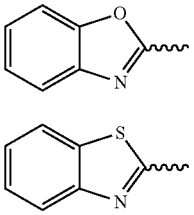 |
| Ar56 | 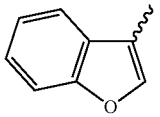 |
| Ar57 | 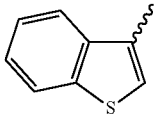 |
| Ar58 | 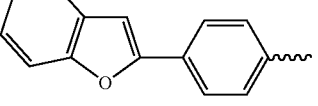 |
| Ar59 | 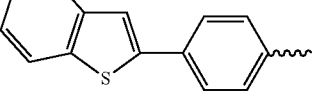 |
| Ar60 | 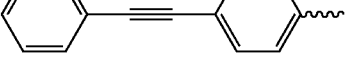 |
| Ar61 | 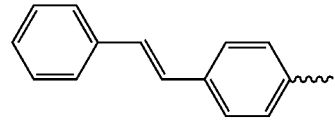 |
| Ar62 | 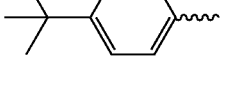 |
| Ar63 | 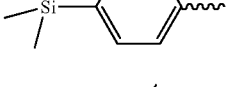 |
| Ar64 | 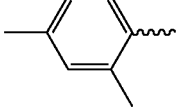 |
| Ar65 | 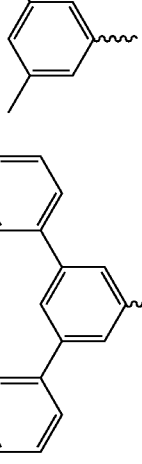 |
| Ar66 | 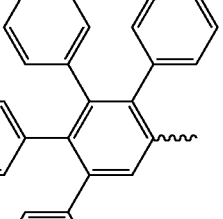 |
| Ar67 | 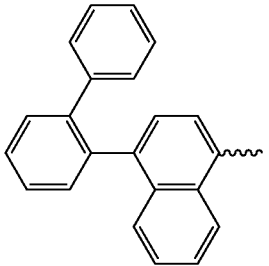 |
| Ar68 | 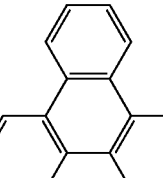 |
| Ar69 | 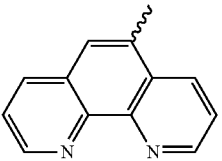 |
| Ar70 | |
| Ar71 | |

TABLE 1-continued
| Ar | Chemical Structure of substituent |
|---|---|
| Ar72 | 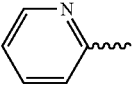 |
| Ar73 | 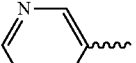 |
| Ar74 | 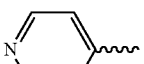 |
| Ar75 | 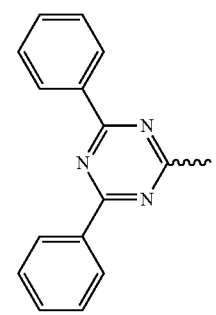 |
| Ar76 | 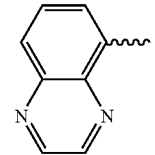 |
| Ar77 | 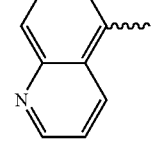 |
| Ar78 | 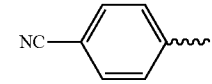 |
| Ar79 | 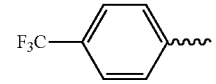 |
| Ar80 | 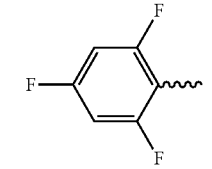 |
| Ar81 | 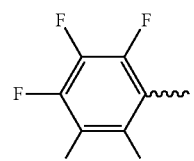 |
| Ar82 | 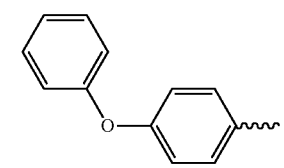 |
| Ar83 | 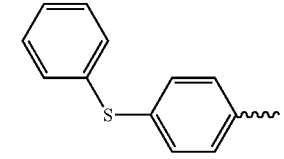 |
| Ar84 | 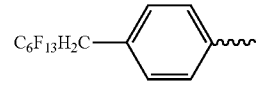 |
| Ar85 | 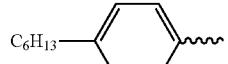 |
| Ar86 | 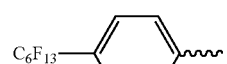 |
| Ar87 | 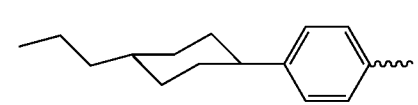 |
| Ar88 | 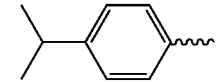 |
| Ar89 | 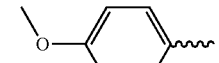 |
| Ar90 | 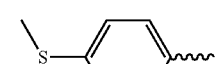 |
| Ar91 | |
| Ar92 | |
In some embodiments, the electroactive material is selected from Compounds 1 to Compound 38.

Compound 1
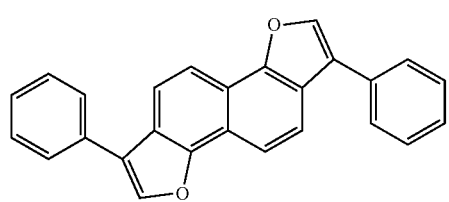
Compound 2
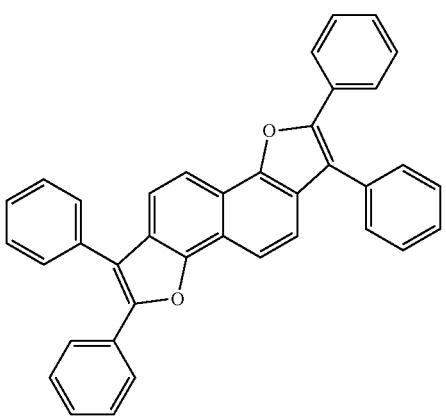
Compound 3
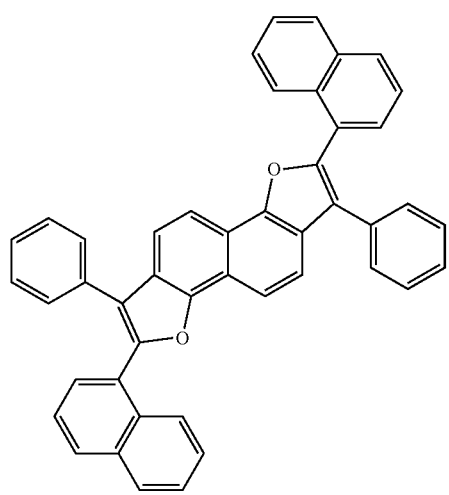
Compound 4
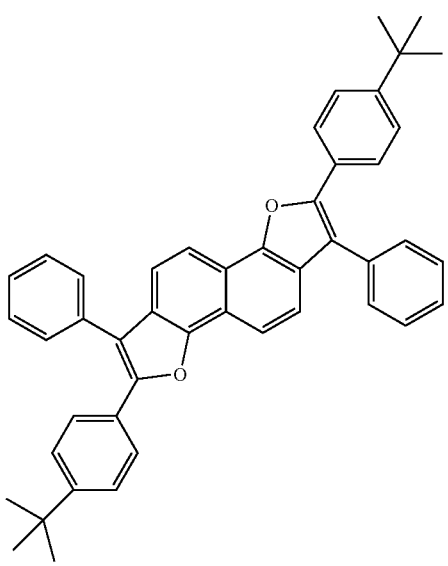
Compound 5
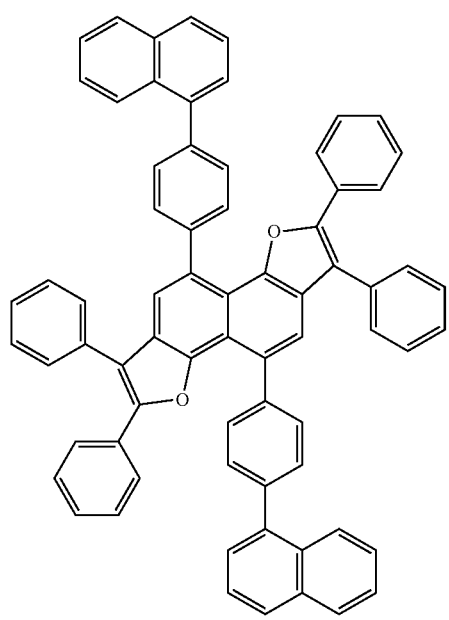
Compound 6
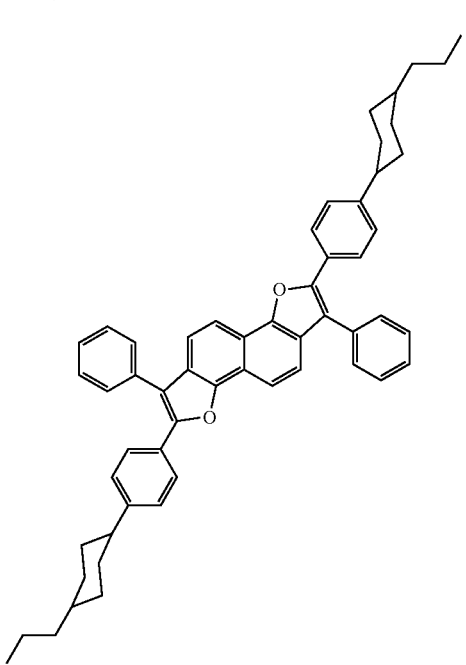

-continued
Compound 7
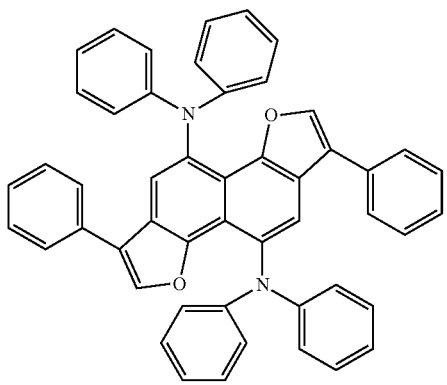
Compound 8
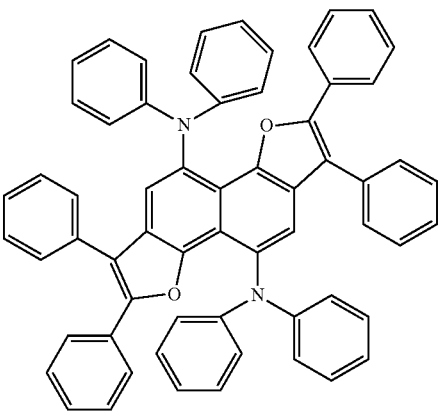
Compound 9
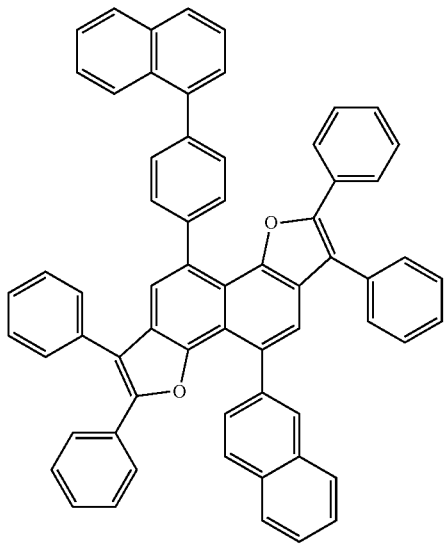
Compound 10
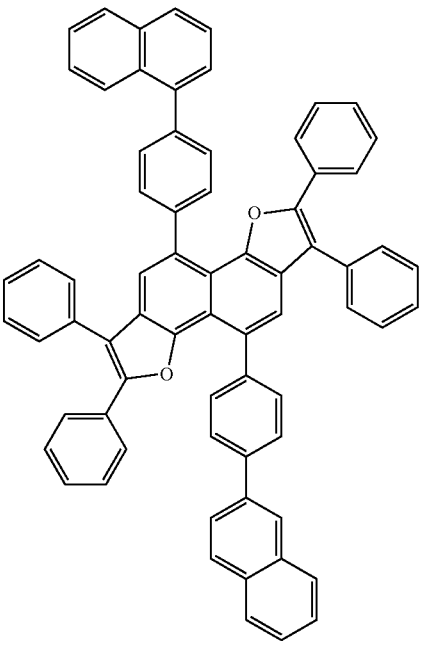
Compound 11
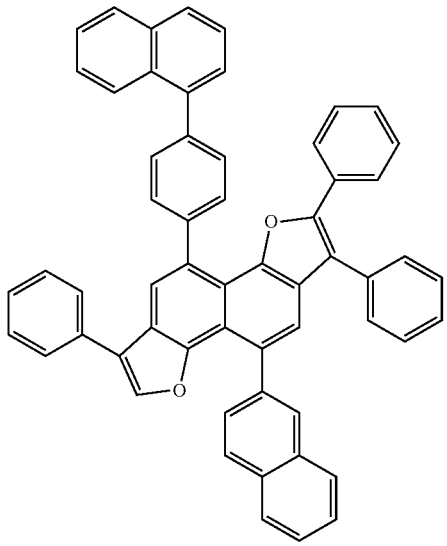
Compound 12
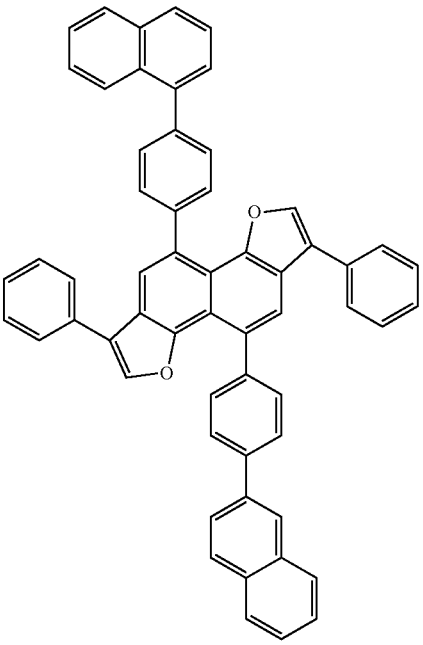

Compound 13
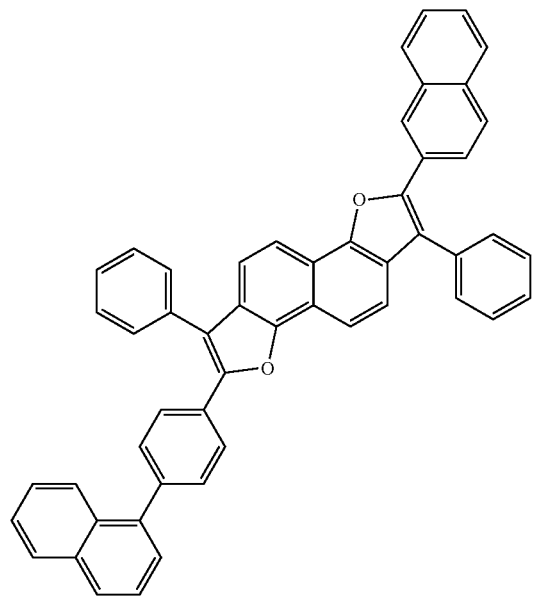
Compound 14
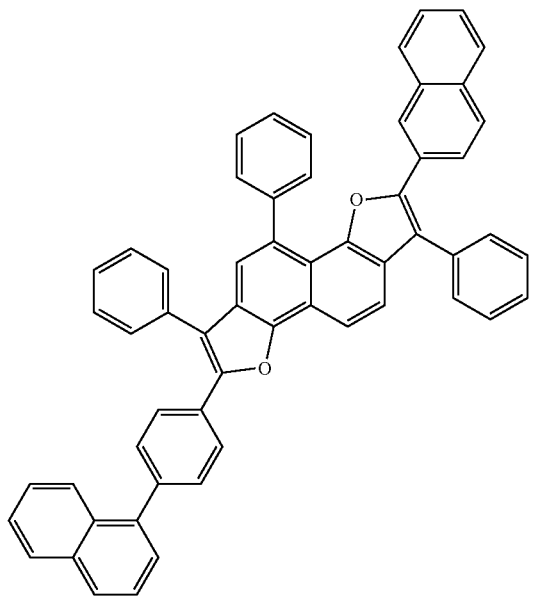
Compound 15
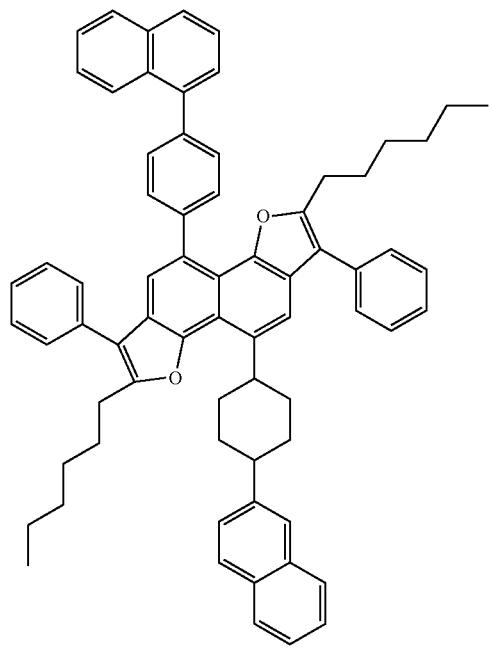
Compound 16
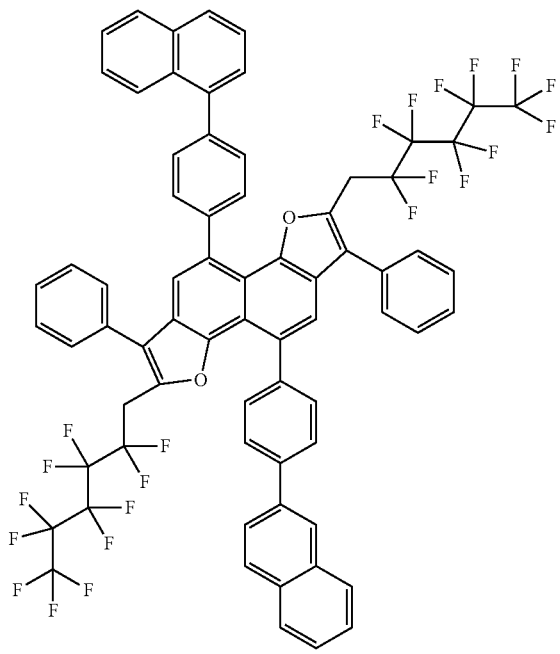

-continued
Compound 17
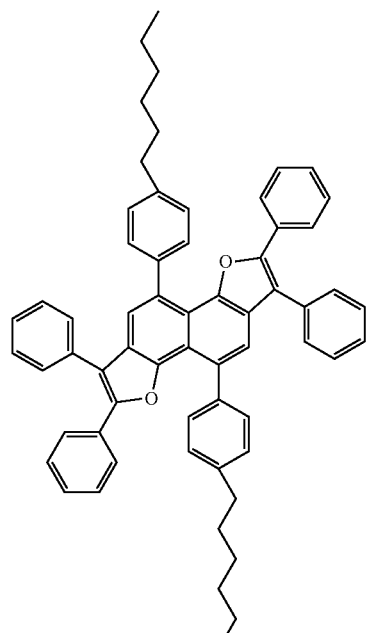
Compound 18
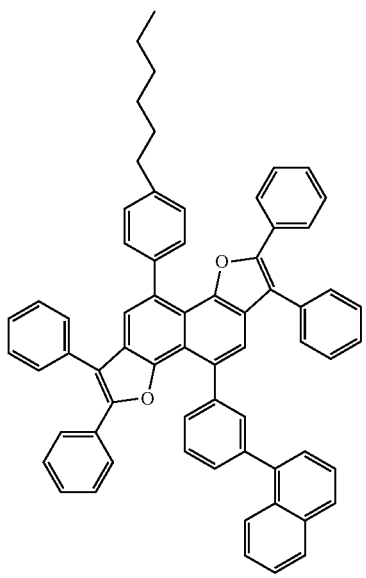
Compound 19
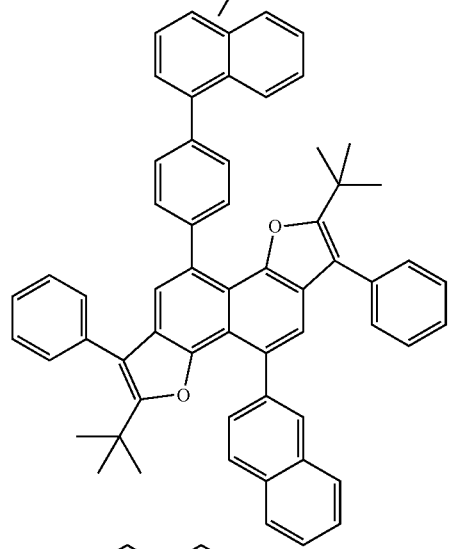
Compound 20
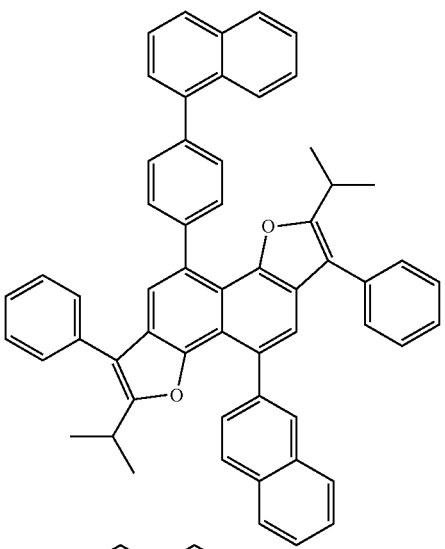
Compound 21
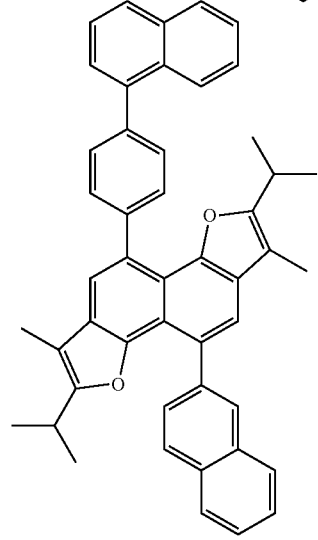
Compound 21
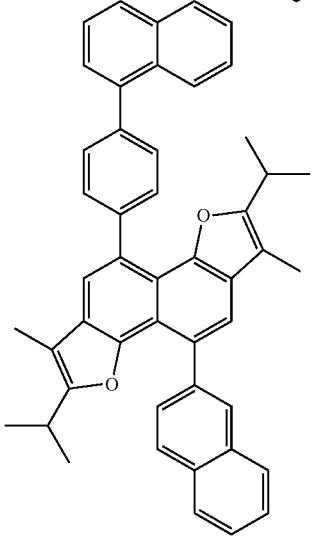

-continued
Compound 22
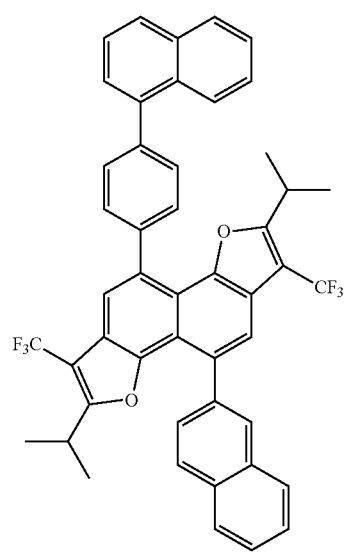
Compound 23
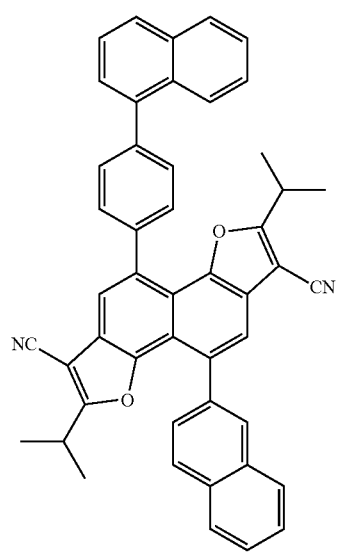
Compound 24
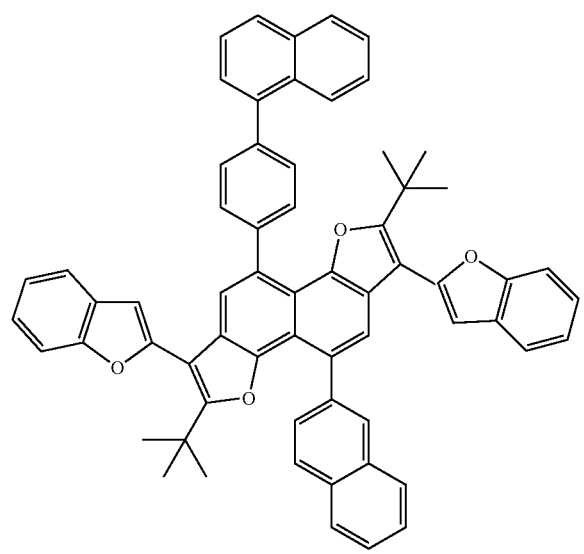
Compound 25
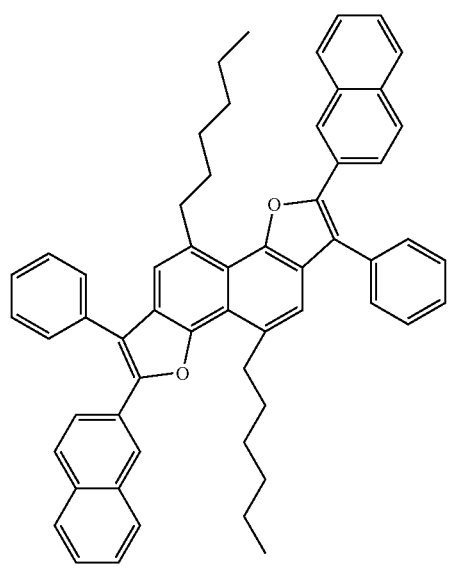

-continued
Compound 26
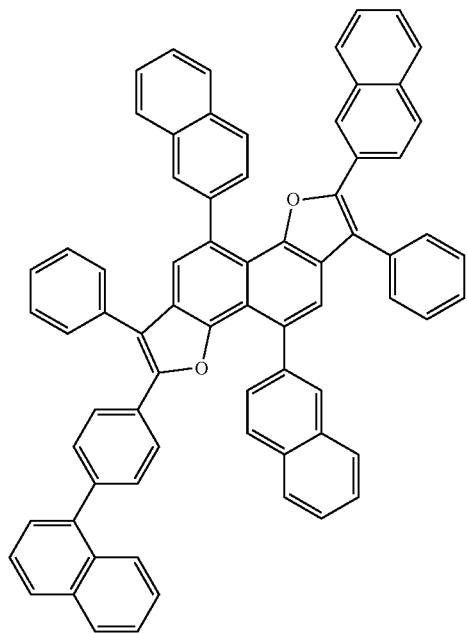
Compound 27
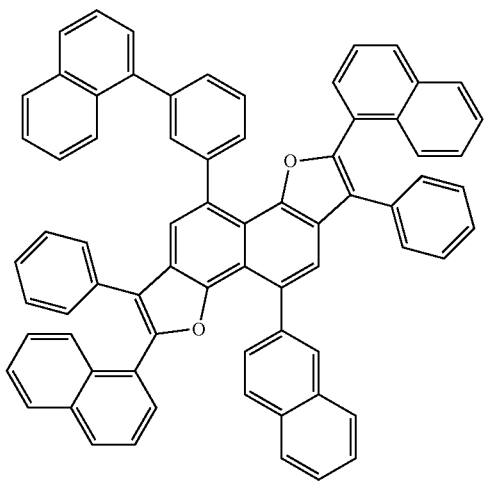
Compound 28
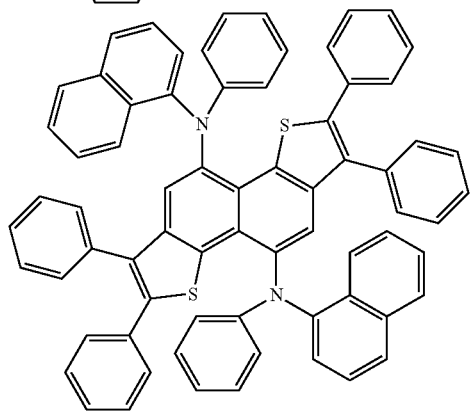
Compound 29
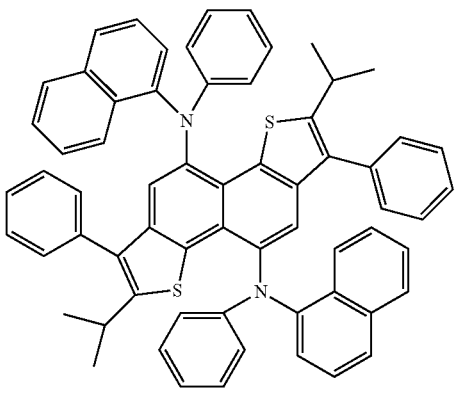
Compound 30
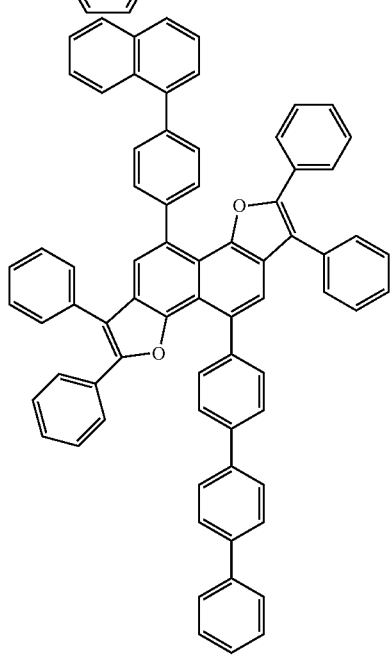
Compound 31
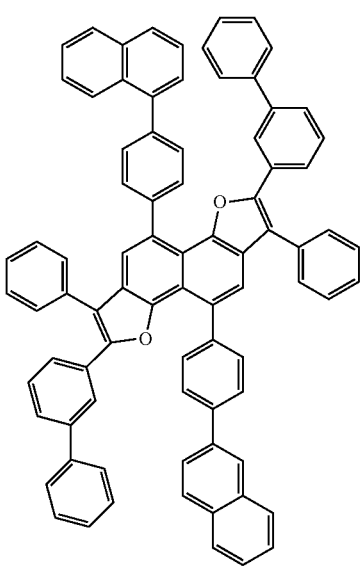

Compound 32
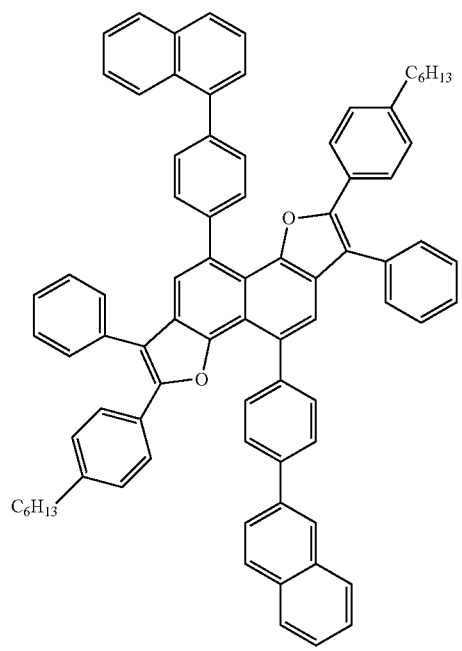
Compound 33
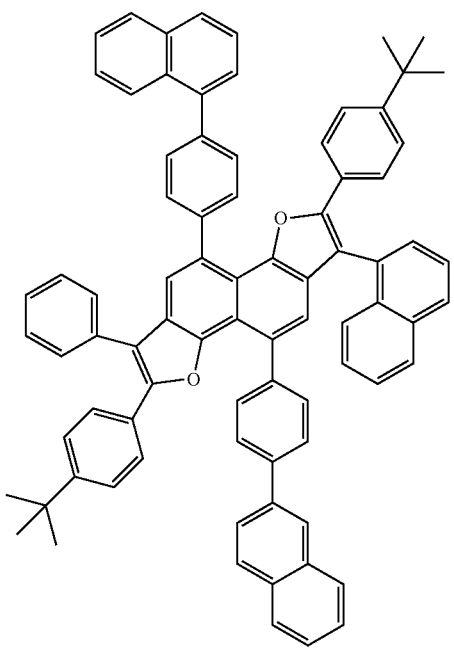
Compound 34
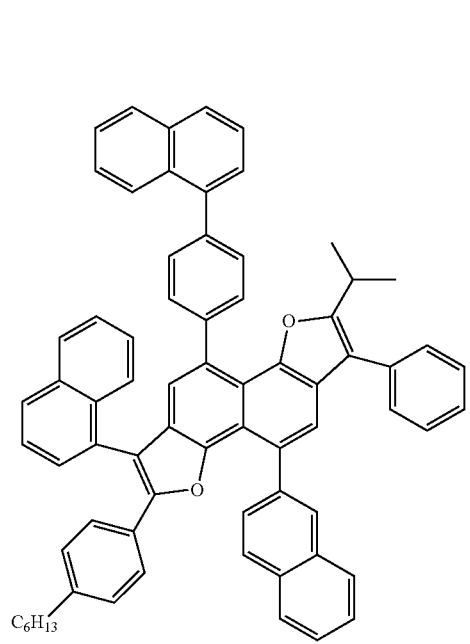
Compound 35
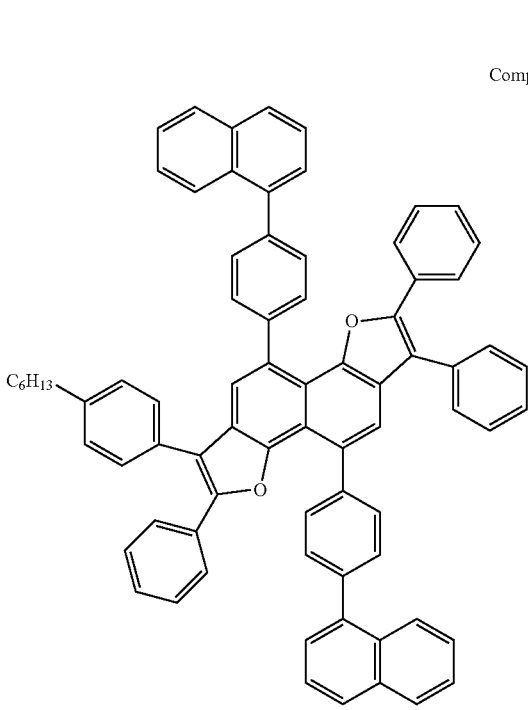

-continued

Compound 36

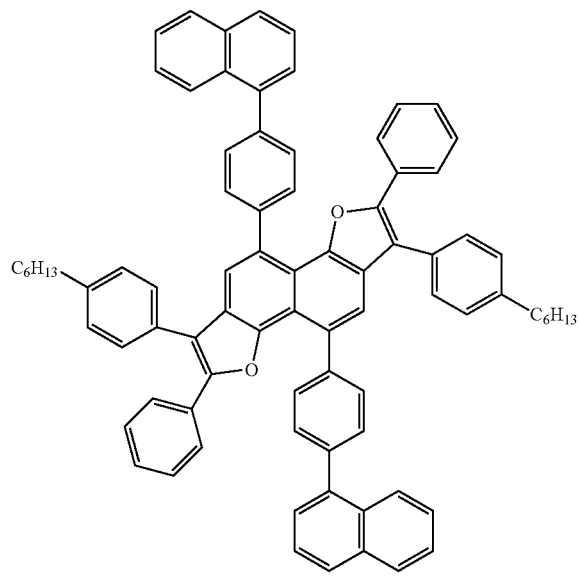

Compound 37

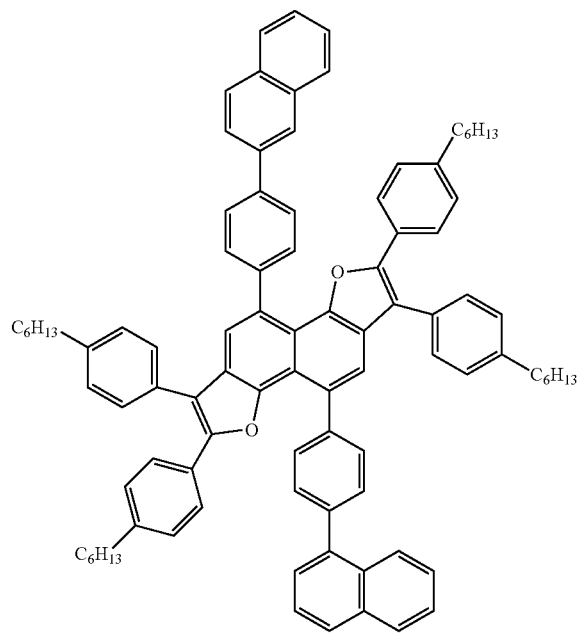

Compound 38

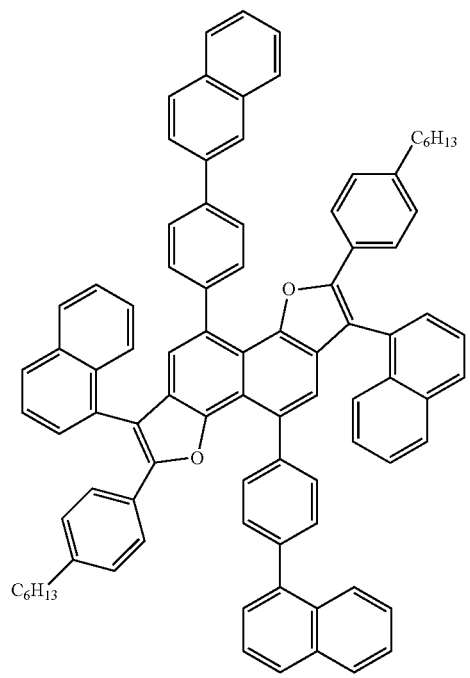

The electroactive materials described herein, can be prepared using standard synthetic techniques, as illustrated in the Examples.

3. Polymers

In some embodiments, the compounds having Formula I are polymerized to form polymeric electroactive materials. In some embodiments, the polymer has at least one monomeric unit selected from the group consisting of Formula II, Formula III, or combinations thereof.

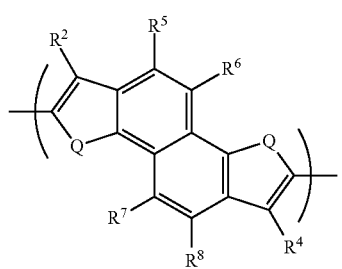

Formula II

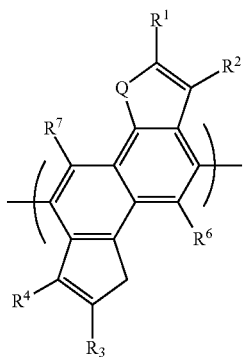

Formula III

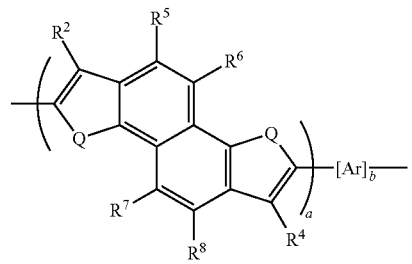

Formula IV

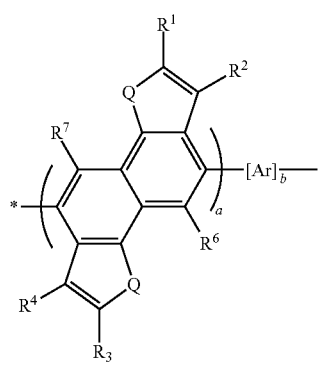

Formula V wherein:

Q is the same or different at each occurrence and is independently selected from the group consisting of O, S, SO, $SO_2$, Se, Te, NR, BR, PR, PO, $PO_2$, and $SiR_2$;

R is the same or different at each occurrence and is independently selected from the group consisting of hydrogen, alkyl, aryl, alkenyl, and alkynyl; and $R^1$ through $R^8$ are the same or different and are independently selected from the group consisting of hydrogen, alkyl, aryl, halogen, hydroxyl, aryloxy, alkoxy, alkenyl, alkynyl, amino, alkylthio, phosphino, silyl, —COR, —COOR, —$PO_3R_2$, —$OPO_3R_2$, and CN.

In some embodiments of Formulae II and III, Q is O or S. In some embodiments of Formula II, Q is O.

In some embodiments of Formulae II and III, at least one of $R^2$ and $R^4$ is not hydrogen. In some embodiments, at least one of $R^2$ and $R^4$ is selected from the group consisting of alkyl, aryl, and diarylamino. In some embodiments, $R^2$ and $R^4$ are the same.

In some embodiments of Formulae II, at least one of $R^5$, $R^6$, $R^7$, and $R^8$ is not hydrogen. In some embodiments, at least one of $R^5$, $R^6$, $R^7$, and $R^8$ is selected from the group consisting of alkyl, aryl, and diarylamino. In some embodiments, $R^5$ and $R^8$ are the same. In some embodiments, $R^6$ and $R^7$ are the same.

In some embodiments of Formula III, at least one of $R^1$ and $R^3$ is not hydrogen. In some embodiments, at least one of $R^1$ and $R^3$ is selected from the group consisting of alkyl, aryl, and diarylamino. In some embodiments, $R^1$ and $R^3$ are the same.

In some embodiments of Formula III, at least one of $R^6$ and $R^7$ is not hydrogen. In some embodiments, at least one of $R^6$ and $R^7$ is selected from the group consisting of alkyl, aryl, and diarylamino. In some embodiments, $R^6$ and $R^7$ are the same.

In some embodiments, the polymer is a homopolymer of Formula II or Formula III, having two or more monomeric units. In some embodiments, the polymer is a copolymer of two or more monomeric units having Formula II with different substituents. In some embodiments, the polymer is a copolymer of two or more monomeric units having Formula III with different substituents. In some embodiments, the polymer is a copolymer having monomeric units of Formula II and monomeric units of Formula III.

In some embodiments, the polymer is a copolymer having Formula IV or V:

wherein:

Ar is the same or different at each occurrence and is an aromatic unit;

Q is the same or different at each occurrence and is independently selected from the group consisting of O, S, SO, $SO_2$, Se, Te, NR, BR, PR, PO, $PO_2$, and $SiR_2$;

R is the same or different at each occurrence and is independently selected from the group consisting of hydrogen, alkyl, aryl, alkenyl, and alkynyl;

$R^1$ through $R^8$ are the same or different and are independently selected from the group consisting of hydrogen, alkyl, aryl, halogen, hydroxyl, aryloxy, alkoxy, alkenyl, alkynyl, amino, alkylthio, phosphino, silyl, —COR, —COOR, —$PO_3R_2$, —$OPO_3R_2$, and CN; and a and b represent mole fractions, such that a+b=1.

The copolymers can be random, alternating, or block copolymers.

Ar is an aromatic unit. In some embodiments, Ar has from 1-5 aromatic rings, which can be joined together by one or more bonds, or fused together. In some embodiments, Ar is selected from the group consisting of Ar1 through Ar 92 in Table 1, where the groups have a second point of attachment on one of the aromatic rings. In some embodiments, Ar is selected from the group consisting of phenylene, naphthylene, biphenylene, binaphthylene, anthracenylene, fluorenylene, diarylamine and combinations thereof. The diarylamine monomeric unit is joined to the polymer backbone via the nitrogen and a carbon on one of the aryl groups. In some embodiments, Ar is further substituted with one or more groups selected from the group consisting of alkyl, aryl, and diarylamino. In some embodiments, Ar is the same at each occurrence. In some embodiments, two different Ar units are present.

In some embodiments of Formulae III, Q is O or S. In some embodiments of Formulae III, Q is O.

In some embodiments of Formulae IV and V, at least one of $R^2$ and $R^4$ is not hydrogen. In some embodiments, at least one of $R^2$ and $R^4$ is selected from the group consisting of alkyl, aryl, and diarylamino. In some embodiments, $R^2$ and $R^4$ are the same.

In some embodiments of Formula IV, at least one of $R^5$, $R^6$, $R^7$, and $R^8$ is not hydrogen. In some embodiments, at least one of $R^5$, $R^6$, $R^7$, and $R^8$ is selected from the group consisting of alkyl, aryl, and diarylamino. In some embodiments, $R^5$ and $R^8$ are the same. In some embodiments, $R^6$ and $R^7$ are the same.

In some embodiments of Formula V, at least one of $R^1$ and $R^3$ is not hydrogen. In some embodiments, at least one of $R^1$ and $R^3$ is selected from the group consisting of alkyl, aryl, and diarylamino. In some embodiments, $R^1$ and $R^3$ are the same.

In some embodiments of Formula V, at least one of $R^6$ and $R^7$ is not hydrogen. In some embodiments, at least one of $R^6$ and $R^7$ is selected from the group consisting of alkyl, aryl, and diarylamino. In some embodiments, $R^6$ and $R^7$ are the same.

In some embodiments of Formulae IV and V, a is at least 0.3. In some embodiments, a is at least 0.5. In some embodiments, a is at least 0.8. In some embodiments, a is 0.3 to 0.7 and b is 0.3 to 0.7.

The polymers can be made using any technique that will yield a C—C or C—N bond and result in polymerization. A variety of such synthetic techniques are known, such as Suzuki, Yamamoto, Stille, and Hartwig-Buchwald coupling.

In Yamamoto polymerization, for example, monomers having Cl, Br, I, or toslyate functional groups, are added to a solution of a Ni(0) compound in an inert solvent. Typically, a nickel (0) cyclooctadiene complex is used in the presence of a 2,2'-bipyridine in a solvent such as DMF. The reaction is generally carried out at temperatures in the range of 60-80° C., and the resulting polymers isolated using known techniques, such as precipitation. This has been described in Yamamoto, Progress in Polymer Science, Vol. 17, p 1153 (1992)

In Suzuki polymerization, for example, monomers having boronic acid functional groups are polymerized with monomers having halide or tosylate functional groups in coupling reactions using Pd(0) catalysts. Alternatively, monomers having both types of functional groups can be used. The monomers may be commercially available, or can be prepared using known synthetic procedures. For example, monomers having bromine functional groups can be synthesized by bromination of an aromatic compound in chloroform. Monomers having boronic acid functional groups can be synthesized, for example, by reaction a bromo-aromatic compound with an organolithium reagent, then quenching the reaction with trimethylborate.

Some examples of polymers having one of Formulae II through V include, but are not limited to Compounds 39-44 below:

Compound 39

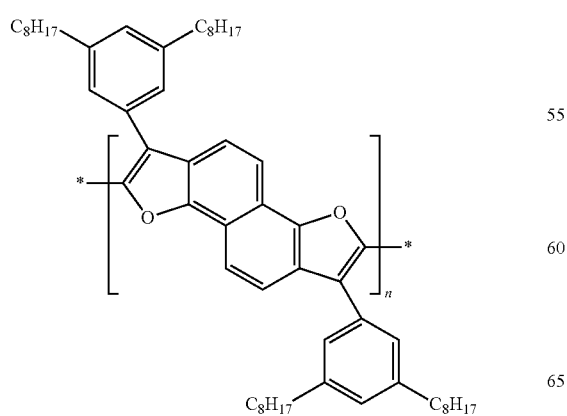

Compound 40

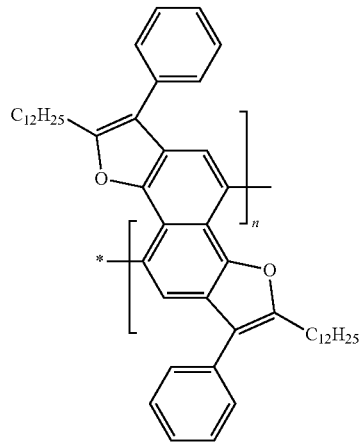

Compound 41

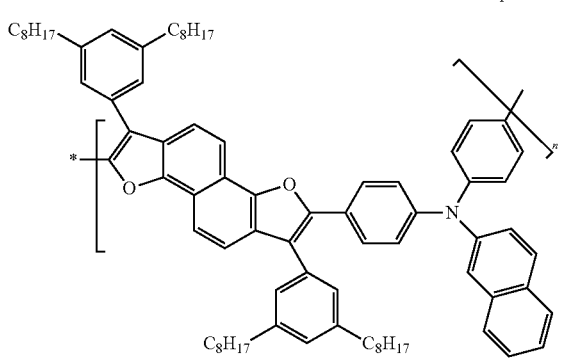

Compound 42

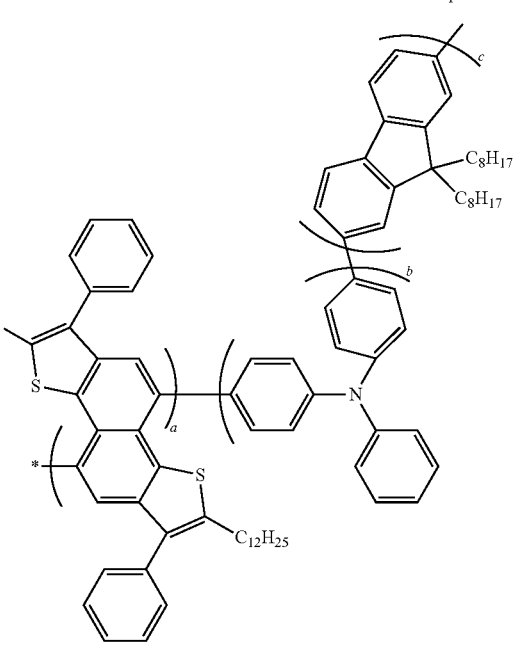

Compound 43

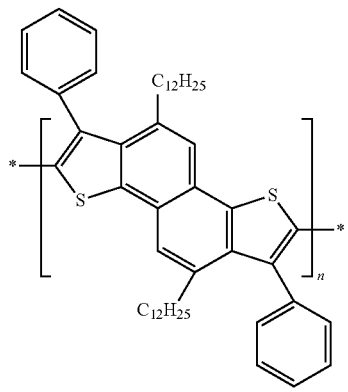

Compound 44

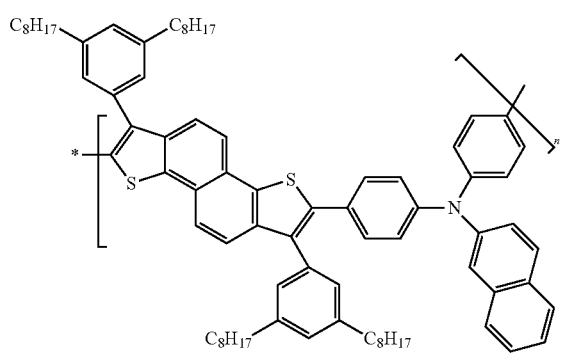

4. Devices

In some embodiments, an organic electronic device comprises a first electrical contact, a second electrical contact and an electroactive layer therebetween, the electroactive layer comprising an electroactive material selected from the group consisting of a compound having Formula I and a polymer having at least one monomeric unit selected from the group consisting of Formula II, Formula III, and combinations thereof.

Organic electronic devices that may benefit from having one or more layers comprising the electroactive materials described herein include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode).

One illustration of an organic electronic device structure is shown in FIG. 1. The device 100 has a first electrical contact layer, an anode layer 110 and a second electrical contact layer, a cathode layer 160, and a photoactive layer 140 between them. Adjacent to the anode is a buffer layer 120. Adjacent to the buffer layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160.

In one embodiment, the different layers have the following range of thicknesses: anode 110, 500-5000 Å, in one embodiment 1000-2000 Å; buffer layer 120, 50-2000 Å, in one embodiment 200-1000 Å; hole transport layer 120, 50-2000 Å, in one embodiment 200-1000 Å; photoactive layer 130, 10-2000 Å, in one embodiment 100-1000 Å; layer 140, 50-2000 Å, in one embodiment 100-1000 Å; cathode 150, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used.

In some embodiments, the device comprises at least one electroactive layer comprising an electroactive material selected from the group consisting of a compound having Formula I and a polymer having at least one monomeric unit selected from the group consisting of Formula II, Formula III, and combinations thereof.

The electroactive materials described herein can be used as charge transport material, as photoactive material, or as a host for another photoactive material.

a. Photoactive Layer

The electroactive materials described herein are particularly suited for use in the photoactive layer 140. They can be present alone and function as the photoactive material, or they can be present as either a host or dopant. The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material. The term "host material" is intended to mean a material, usually in the form of a layer, to which a dopant may or may not be added. The host material may or may not have electronic characteristic(s) or the ability to emit, receive, or filter radiation.

In some embodiments, they function as the photoactive material. In some embodiments, when used as emissive materials, they exhibit a blue, blue-green or green color. They can be used alone, in combination with other luminescent materials, or as a dopant in a host material. In some embodiments, the electroactive materials are used as a host material for one or more other emissive materials. They are particularly suited as a host for blue dopants.

In some embodiments, the electroactive materials described herein are used as a dopant in a host material. In some embodiments, the host is a bis-condensed cyclic aromatic compound.

In some embodiments, the host is an anthracene derivative compound. In some embodiments the compound has the formula:

An-L-An where:
An is an anthracene moiety;
L is a divalent connecting group.

In some embodiments of this formula, L is a single bond, —O—, —S—, —N(R)—, or an aromatic group. In some embodiments, An is a mono- or diphenylanthryl moiety.

In some embodiments, the host has the formula:

A-An-A where:
An is an anthracene moiety;
A is an aromatic group.

In some embodiments, the host is a diarylanthracene. In some embodiments the compound is symmetrical and in some embodiments the compound is non-symmetrical.

In some embodiments, the host has the formula:

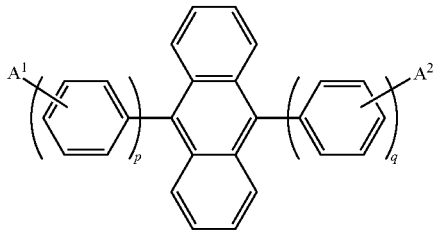

where:

$A^1$ and $A^2$ are the same or different at each occurrence and are selected from the group consisting of H, an aromatic group, and an alkenyl group, or A may represent one or more fused aromatic rings;

p and q are the same or different and are an integer from 1-3.

In some embodiments, the anthracene derivative is non-symmetrical. In some embodiments, p=2 and q=1. In some embodiments, at least one of $A^1$ and $A^2$ is a naphthyl group.

In some embodiments, the host is selected from the group consisting of

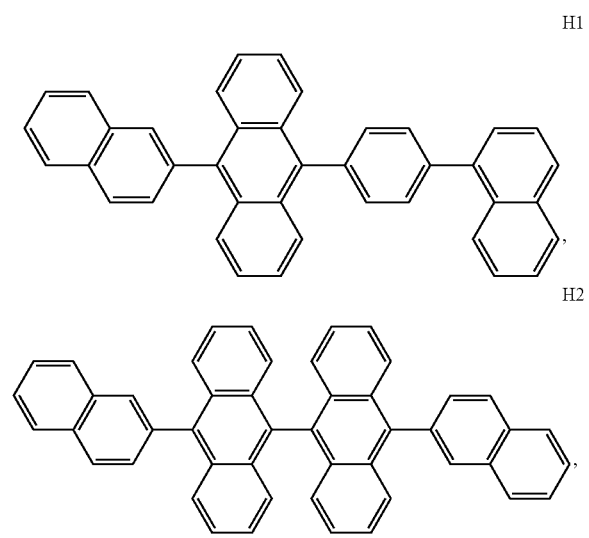

and combinations thereof.

b. Other Device Layers

The other layers in the device can be made of any materials which are known to be useful in such layers.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also comprise an organic material such as polyaniline as described in "Flexible light-emitting diodes made from soluble conducting polymer," Nature vol. 357, pp 477 479 (11 June 1992). At least one of the anode and cathode should be at least partially transparent to allow the generated light to be observed.

The buffer layer 120 comprises buffer material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device The buffer layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The buffer layer can comprise charge transfer compounds, and the like, such as copper phthalocyanine and the tetrathiafulvalene-tetracyanoquinodimethane system (TTF-TCNQ).

In some embodiments, the buffer layer comprises at least one electrically conductive polymer and at least one fluorinated acid polymer.

In some embodiments, the buffer layer is made from an aqueous dispersion of an electrically conducting polymer and a colloid-forming polymeric acid. Such materials have been described in, for example, published U.S. patent applications 2004-0102577, 2004-0127637, and 2005-0205860.

The hole transport layer 130 is a charge transport layer which facilitates the migration of positive charges. In some embodiments, the hole transport layer comprises the new electroactive material described herein. In some embodiments, the hole transport layer consists essentially of the new electroactive material described herein. In some embodiments, the hole transport layer comprises the new electroactive polymer described herein. In some embodiments, the hole transport layer consists essentially of the new electroactive polymer described herein.

Examples of other hole transport materials for the hole transport layer have been summarized for example, in Kirk-Othmer Encyclopedia of Chemical Technology, Fourth Edition, Vol. 18, p. 837-860, 1996, by Y. Wang. Both hole transporting small molecules and polymers can be used. Commonly used hole transporting molecules include, but are not limited to: 4,4',4"-tris(N,N-diphenyl-amino)-triphenylamine (TDATA); 4,4',4"-tris(N-3-methylphenyl-N-phenylamino)-triphenylamine (MTDATA); N,N'-diphenyl-N,N'-bis(3-methylphenyl)-[1,1'-biphenyl]-4,4'-diamine (TPD); 4,4'-bis(carbazol-9-yl)biphenyl (CBP); 1,3-bis(carbazol-9-yl)benzene (mCP); 1,1-bis[(di-4-tolylamino) phenyl]cyclohexane (TAPC); N,N'-bis(4-methylphenyl)-N,N'-bis(4-ethylphenyl)-[1,1'-(3,3'-dimethyl)biphenyl]-4,4'-diamine (ETPD); tetrakis-(3-methylphenyl)-N,N,N',N'-2,5-phenylenediamine (PDA); α-phenyl-4-N,N-diphenylaminostyrene (TPS); p-(diethylamino)benzaldehyde diphenylhydrazone (DEH); triphenylamine (TPA); bis[4-(N,N-diethylamino)-2-methylphenyl](4-methylphenyl)methane (MPMP); 1-phenyl-3-[p-(diethylamino)styryl]-5-[p-(diethylamino)phenyl]pyrazoline (PPR or DEASP); 1,2-trans-bis(9H-carbazol-9-yl)cyclobutane (DCZB); N,N,N',N'-tetrakis(4-methylphenyl)-(1,1'-biphenyl)-4,4'-diamine (TTB); N,N'-bis(naphthalen-1-yl)-N,N'-bis-(phenyl)benzidine (α-NPB); and porphyrinic compounds, such as copper phthalocyanine. Commonly used hole transporting polymers include, but are not limited to, polyvinylcarbazole, (phenylmethyl)polysilane, poly(dioxythiophenes), polyanilines, and polypyrroles. It is also possible to obtain hole transporting polymers by doping hole transporting molecules such as those mentioned above into polymers such as polystyrene and polycarbonate.

In some embodiments, the hole transport layer comprises a hole transport polymer. In some embodiments, the hole transport polymer is a distyrylaryl compound. In some embodiments, the aryl group is has two or more fused aromatic rings. In some embodiments, the aryl group is an acene. The term "acene" as used herein refers to a hydrocarbon parent component that contains two or more ortho-fused benzene rings in a straight linear arrangement.

In some embodiments, the hole transport polymer is an arylamine polymer. In some embodiments, it is a copolymer of fluorene and arylamine monomers.

In some embodiments, the polymer has crosslinkable groups. In some embodiments, crosslinking can be accomplished by a heat treatment and/or exposure to UV or visible radiation. Examples of crosslinkable groups include, but are not limited to vinyl, acrylate, perfluorovinylether, 1-benzo-3,4-cyclobutane, siloxane, and methyl esters. Crosslinkable polymers can have advantages in the fabrication of solution-process OLEDs. The application of a soluble polymeric material to form a layer which can be converted into an insoluble film subsequent to deposition, can allow for the fabrication of multilayer solution-processed OLED devices free of layer dissolution problems.

Examples of crosslinkable polymers can be found in, for example, published US patent application 2005-0184287 and published PCT application WO 2005/052027.

In some embodiments, the hole transport layer comprises a polymer which is a copolymer of 9,9-dialkylfluorene and triphenylamine. In some embodiments, the polymer is a copolymer of 9,9-dialkylfluorene and 4,4'-bis(diphenylamino)biphenyl. In some embodiments, the polymer is a copolymer of 9,9-dialkylfluorene and TPB. In some embodiments, the polymer is a copolymer of 9,9-dialkylfluorene and NPB. In some embodiments, the copolymer is made from a third comonomer selected from (vinylphenyl)diphenylamine and 9,9-distyrylfluorene or 9,9-di(vinylbenzyl)fluorene.

The electron transport layer 150 is a charge transport layer which facilitates the migration of negative charges. In some embodiments, the electron transport layer comprises the new electroactive material described herein. In some embodiments, the electron transport layer comprises the new electroactive copolymer described herein. In some embodiments, the electron transport layer consists essentially of the new electroactive copolymer described herein.

The electron transport layer 150 is a layer which facilitates migration of negative charges through the thickness of the layer with relative efficiency and small loss of charge. Examples of electron transport materials which can be used in the optional electron transport layer 140, include metal chelated oxinoid compounds, such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer 150 and the cathode layer 160 to lower the operating voltage. This layer, not shown, may be referred to as an electron injection layer.

c. Device Fabrication

The device layers can be formed by any deposition technique, or combinations of techniques, including vapor deposition, liquid deposition, and thermal transfer.

In some embodiments, the device is fabricated by liquid deposition of the buffer layer, the hole transport layer, and the photoactive layer, and by vapor deposition of the anode, the electron transport layer, an electron injection layer and the cathode.

The buffer layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is selected from the group consisting of alcohols, ketones, cyclic ethers, and polyols. In one embodiment, the organic liquid is selected from dimethylacetamide ("DMAc"), N-methylpyrrolidone ("NMP"), dimethylformamide ("DMF"), ethylene glycol ("EG"), aliphatic alcohols, and mixtures thereof. The buffer material can be present in the liquid medium in an amount from 0.5 to 10 percent by weight. Other weight percentages of buffer material may be used depending upon the liquid medium. The buffer layer can be applied by any continuous or discontinuous liquid deposition technique. In one embodiment, the buffer layer is applied by spin coating. In one embodiment, the buffer layer is applied by ink jet printing. After liquid deposition, the liquid medium can be removed in air, in an inert atmosphere, or by vacuum, at room temperature or with heating. In one embodiment, the layer is heated to a temperature less than 275° C. In one embodiment, the heating temperature is between 100° C. and 275° C. In one embodiment, the heating temperature is between 100° C. and 120° C. In one embodiment, the heating temperature is between 120° C. and 140° C. In one embodiment, the heating temperature is between 140° C. and 160° C. In one embodiment, the heating temperature is between 160° C. and 180° C. In one embodiment, the heating temperature is between 180° C. and 200° C. In one embodiment, the heating temperature is between 200° C. and 220° C. In one embodiment, the heating temperature is between 190° C. and 220° C. In one embodiment, the heating temperature is between 220° C. and 240° C. In one embodiment, the heating temperature is between 240° C. and 260° C. In one embodiment, the heating temperature is between 260° C. and 275° C. The heating time is dependent upon the temperature, and is generally between 5 and 60 minutes. In one embodiment, the final layer thickness is between 5 and 200 nm. In one embodiment, the final layer thickness is between 5 and 40 nm. In one embodiment, the final layer thickness is between 40 and 80 nm. In one embodiment, the final layer thickness is between 80 and 120 nm. In one embodiment, the final layer thickness is between 120 and 160 nm. In one embodiment, the final layer thickness is between 160 and 200 nm.

The hole transport layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is an aromatic solvent. In one embodiment, the organic liquid is selected from chloroform, dichloromethane, toluene, xylene, mesitylene, anisole, and mixtures thereof. The hole transport material can be present in the liquid medium in a concentration of 0.2 to 2 percent by weight. Other weight percentages of hole transport material may be used depending upon the liquid medium. The hole transport layer can be applied by any continuous or discontinuous liquid deposition technique. In one embodiment, the hole transport layer is applied by spin coating. In one embodiment, the hole transport layer is applied by ink jet printing. After liquid deposition, the liquid medium can be removed in air, in an inert atmosphere, or by vacuum, at room temperature or with heating. In one embodiment, the layer is heated to a temperature of 300° C. or less. In one embodiment, the heating temperature is between 170° C. and 275° C. In one embodiment, the heating temperature is between 170° C. and 200° C. In one embodiment, the heating temperature is between 190° C. and 220° C. In one embodiment, the heating temperature is between 210° C. and 240° C. In one embodiment, the heating temperature is between 230° C. and 270° C. In one embodiment, the heating temperature is between 270° C. and 300° C. The heating time is dependent upon the temperature, and is generally between 5 and 60 minutes. In one embodiment, the final layer thickness is between 5 and 50 nm. In one embodiment, the final layer thickness is between 5 and 15 nm. In one embodiment, the final layer thickness is between 15 and 25 nm. In one embodiment, the final layer thickness is between 25 and 35 nm. In one embodiment, the final layer thickness is between 35 and 50 nm.

The photoactive layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is an aromatic solvent. In one embodiment, the organic solvent is selected from chloroform, dichloromethane, toluene, anisole, 2-butanone, 3-pentanone, butyl acetate, acetone, xylene, mesitylene, chlorobenzene, tetrahydrofuran, diethyl ether, trifluorotoluene, and mixtures thereof. The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In one embodiment, the photoactive layer is applied by spin coating. In one embodiment, the photoactive layer is applied by ink jet printing. After liquid deposition, the liquid medium can be removed in air, in an inert atmosphere, or by vacuum, at room temperature or with heating. Optimal baking conditions depend on the vapor pressure properties of the liquids being removed and their molecular interaction with the liquids. In one embodiment, the deposited layer is heated to a temperature that is greater than the Tg of the material having the highest Tg. In one embodiment, the deposited layer is heated between 10 and 20° C. higher than the Tg of the material having the highest Tg. In one embodiment, the deposited layer is heated to a temperature that is less than the Tg of the material having the lowest Tg. In one embodiment, the heating temperature is at least 10° C. less than the lowest Tg. In one embodiment, the heating temperature is at least 20° C. less than the lowest Tg. In one embodiment, the heating temperature is at least 30° C. less than the lowest Tg. In one embodiment, the heating temperature is between 50° C. and 150° C. In one embodiment, the heating temperature is between 50° C. and 75° C. In one embodiment, the heating temperature is between 75° C. and 100° C. In one embodiment, the heating temperature is between 100° C. and 125° C. In one embodiment, the heating temperature is between 125° C. and 150° C. The heating time is dependent upon the temperature, and is generally between 5 and 60 minutes. In one embodiment, the final layer thickness is between 25 and 100 nm. In one embodiment, the final layer thickness is between 25 and 40 nm. In one embodiment, the final layer thickness is between 40 and 65 nm. In one embodiment, the final layer thickness is between 65 and 80 nm. In one embodiment, the final layer thickness is between 80 and 100 nm.

The electron transport layer can be deposited by any vapor deposition method. In one embodiment, it is deposited by thermal evaporation under vacuum. In one embodiment, the final layer thickness is between 1 and 100 nm. In one embodiment, the final layer thickness is between 1 and 15 nm. In one embodiment, the final layer thickness is between 15 and 30 nm. In one embodiment, the final layer thickness is between 30 and 45 nm. In one embodiment, the final layer thickness is between 45 and 60 nm. In one embodiment, the final layer thickness is between 60 and 75 nm. In one embodiment, the final layer thickness is between 75 and 90 nm. In one embodiment, the final layer thickness is between 90 and 100 nm.

The electron injection layer can be deposited by any vapor deposition method. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C.; 150° C. to 350° C. preferably. The vapor deposition rates given herein are in units of Angstroms per second. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 0.1 and 3 nm. In one embodiment, the final layer thickness is between 0.1 and 1 nm. In one embodiment, the final layer thickness is between 1 and 2 nm. In one embodiment, the final layer thickness is between 2 and 3 nm.

The cathode can be deposited by any vapor deposition method. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C.; 150° C. to 350° C. preferably. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 10 and 10000 nm. In one embodiment, the final layer thickness is between 10 and 1000 nm. In one embodiment, the final layer thickness is between 10 and 50 nm. In one embodiment, the final layer thickness is between 50 and 100 nm. In one embodiment, the final layer thickness is between 100 and 200 nm. In one embodiment, the final layer thickness is between 200 and 300 nm. In one embodiment, the final layer thickness is between 300 and 400 nm. In one embodiment, the final layer thickness is between 400 and 500 nm. In one embodiment, the final layer thickness is between 500 and 600 nm. In one embodiment, the final layer thickness is between 600 and 700 nm. In one embodiment, the final layer thickness is between 700 and 800 nm. In one embodiment, the final layer thickness is between 800 and 900 nm. In one embodiment, the final layer thickness is between 900 and 1000 nm. In one embodiment, the final layer thickness is between 1000 and 2000 nm. In one embodiment, the final layer thickness is between 2000 and 3000 nm. In one embodiment, the final layer thickness is between 3000 and 4000 nm. In one embodiment, the final layer thickness is between 4000 and 5000 nm. In one embodiment, the final layer thickness is between 5000 and 6000 nm. In one embodiment, the final layer thickness is between 6000 and 7000 nm. In one embodiment, the final layer thickness is between 7000 and 8000 nm. In one embodiment, the final layer thickness is between 8000 and 9000 nm. In one embodiment, the final layer thickness is between 9000 and 10000 nm.

EXAMPLES

The concepts described herein will be further described in the following examples, which do not limit the scope of the invention described in the claims.

Example 1

This example illustrates the preparation of electroactive Compound 1.

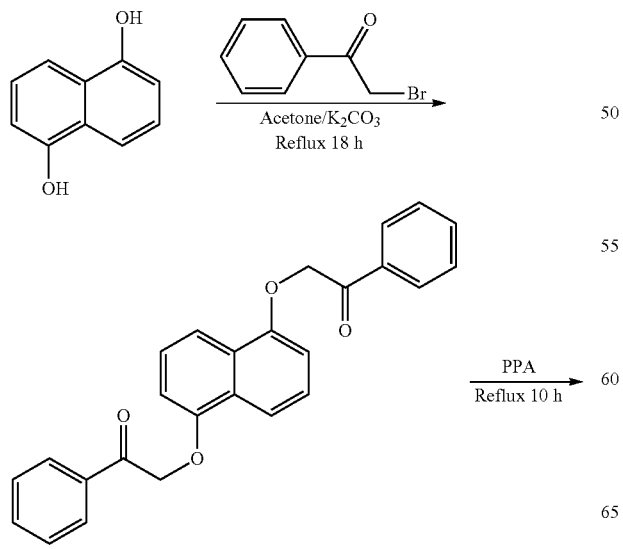

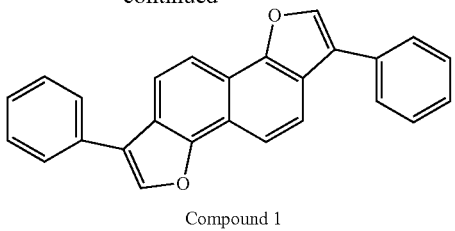

Compound 1 a. Preparation of Intermediate A

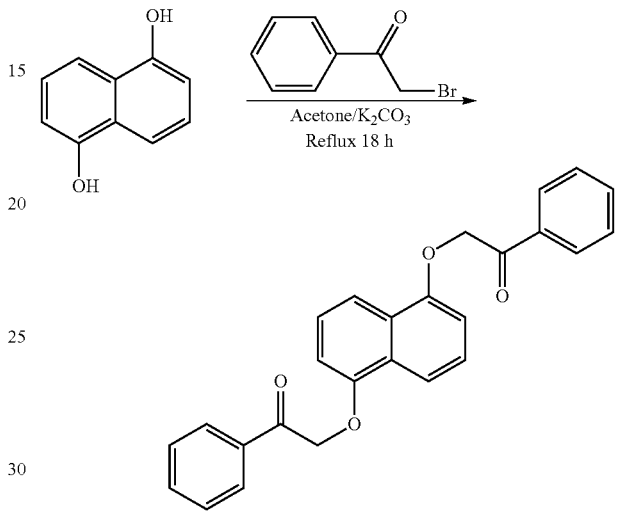

Intermediate A

To a mixture solution of 1,5-dihydroxynaphthalene (99%, Alfer Aesar) (16.0 g, 0.10 mole), bromoacetophenone (Aldrich, 41.8 g, 0.21 mole) in acetone (400 mL) was added potassium carbonate (45 g, 0.33 mole) powder. The mixture was heated to reflux for 18 h. The white solid was formed during the reaction. The solids were filtered off and washed with water, diluted HCl (5%, 200 mL), water (100 mL, 3×), acetone (200 mL) and dried to give Intermediate A, 38.4 g, off-white powder, yield: 97%. EI, MS m/z (%): 396 (100, M$^+$). $C_{26}H_{20}O_4$.

b. Preparation of Compound 1.

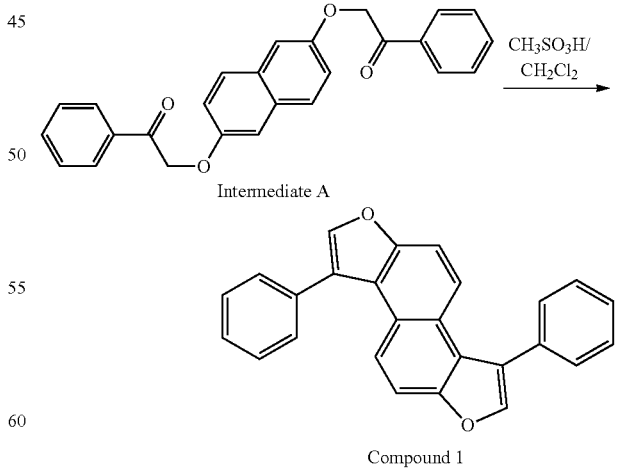

Compound 1

Into a RBF (500 mL) was added Intermediate A from step a (40 g, 0.101 mole), $CH_2Cl_2$ (2300 mL), then added drop wise $CH_3SO_3H$ (50 g, 0.5 mole). The suspension mixture became pink in color then a dark brown solution. It was refluxed for 1 h. TLC (in Hexane:ethyl acetate 10:1) gives a blueish brown color spot (Rf: 0.7), clearly indicated the new material was produced. (Rf: 2,6-dihydroxnaphthalene: 0.01, Rf: 2-bromo-1-phenylethanone: 0.5). It was run through a flash column to get the pure product. Off-white crystals, 28 g, yield 78%. $C_{26}H_{16}O_2$: EI, MS m/z (%): 360 (100, M$^+$).
Example 2
This example illustrates the general steps for the preparation of Compound 2, Compound 5, and Compound 8.
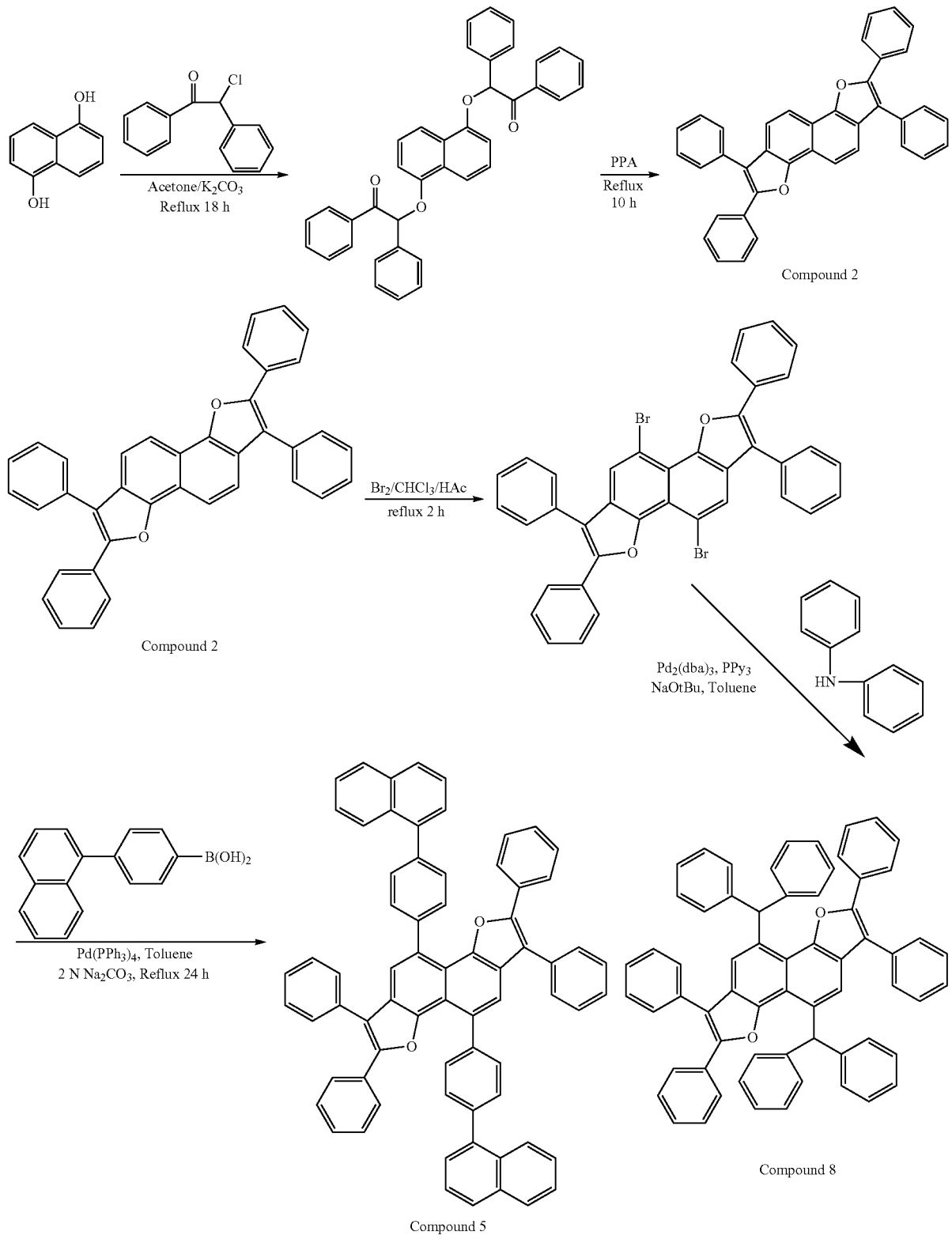

Example 3

This example illustrates the preparation of Compound 2.

a. Preparation of Intermediate B

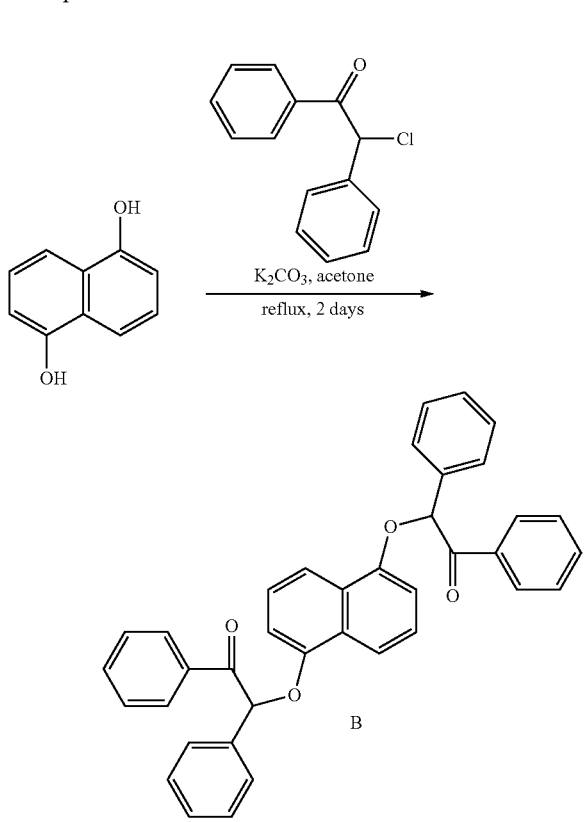

To a mixture solution of 1,5-dihydroxynaphthalene (99%, Alfer Aesar) (14.2 g, 0.086 mole), 2-chloro-2-phenylacetophenone (41.6 g, 0.18 mole) in acetone (350 mL) was added potassium carbonate (53.9 g, 0.39 mole) powder. The mixture was heated to reflux for 18 h. The white solid was formed during the reaction. The solids were filtered off and washed with water, diluted HCl (5%, 200 mL), water (100 mL, 3×), acetone (200 mL) and dried to give Intermediate B, 26.09 g, off white powder, yield: 54%. EI, MS m/z (%): 548 (100, M+). $C_{38}H_{28}O_4$.

b. Preparation of Compound 2

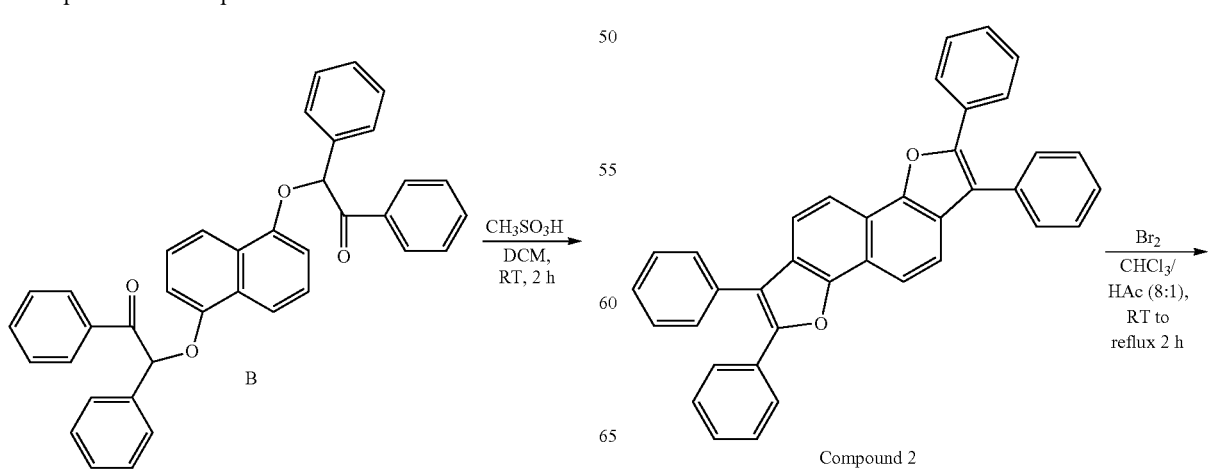

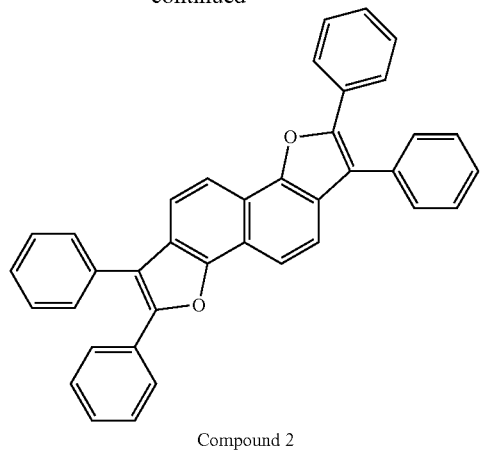

Compound 2

Into a RBF (500 mL) was added Intermediate B (26.06 g, 0.047 mole), $CH_2Cl_2$ (800 mL), cooled down about to 5° C. using ice-water bath. $CH_3SO_3H$ (50 g, 0.5 mole) was added dropwise and keep the temperature below 10° C. The suspension mixture became pink color then dark brown solution. It was stirred at room temperature for 2 h. TLC checked (hex/ $CHCl_3$ 5:1). The mixture was washed with water. The aqueous layer was extracted with $CHCl_3$. The combined organic layers were concentrated and passed through a silica gel column, rinsed with $CHCl_3$ (~8 L, used recycled $CHCl_3$). The purer fractions were collected and concentrated, washed with acetone. The solid was filtered to give 11.39 g, yellow solid. The less purer fractions were also collected and concentrated, washed with acetone. The solid was filtered to give Compound 2, 7.90 g, dark yellow solid. Total yield 79%. Recrystallized (2×) from $CHCl_3$ to give 9.27 g, light yellow crystals, HPLC 100%. $^1$H NMR ($CDCl_3$, ref: δ 7.26 ppm, 500 MHz): δ 8.28-8.26 ppm (d, 2H, J=8.5 Hz), 7.77-7.75 ppm (dd, 4H, J1=7.5 Hz, J2=1.2 Hz), 7.71-7.69 ppm (d, 2H, J=8.5 Hz), 7.61-7.59 ppm (dd, 4H, J1=7.5 Hz, J2=1.2 Hz), 7.54-7.60 ppm (t, 4H, J=7.5 Hz), 7.47-7.44 ppm (tt, 2H, J1=7.5 Hz, J2=1.2 Hz), 7.37-7.34 ppm (tt, 4H, J1=7.5 Hz, J2=1.2 Hz), 7.32-7.28 ppm (tt, 2H, J1=7.5 Hz, J2=1.2 Hz), 7.66 ppm (s, 2H), 7.61-7.60 ppm (dd, 4H, J1=8.5 Hz, J2=1.9 Hz), 7.55-7.45 ppm (m, 8H). $C_{38}H_{24}O_2$: EI, MS m/z (%): 512 (100, M+).

Example 4

This example illustrates the preparation of Compound 8.

a. Preparation of Intermediate C

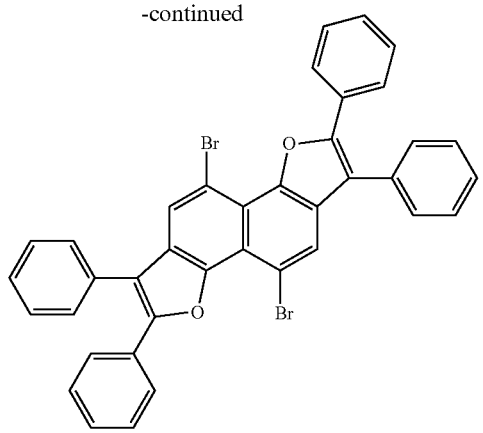

Intermediate C

To a solution of Compound 2 (4.4 g, 0.0085 mole) in CHCl$_3$/HAc (80:10 mL) (not completely dissolved) was added Br$_2$ (2.8 g, 0.017 mole) in CHCl$_3$ (10 mL) slowly at RT. The mixture was stirred overnight (TLC monitored) and then refluxed for 2 h. After cooling down to room temperature, the formed solid was filtered and rinsed several times with CHCl$_3$ and acetone. It was then recrystallized from chloroform to give white solid Intermediate C, 5.64 g, yield: 99%, white solid. C$_{38}$H$_{22}$Br$_2$O$_2$: EI, MS m/z (%): 670 (100, M$^+$).

b. Preparation of Compound 8.

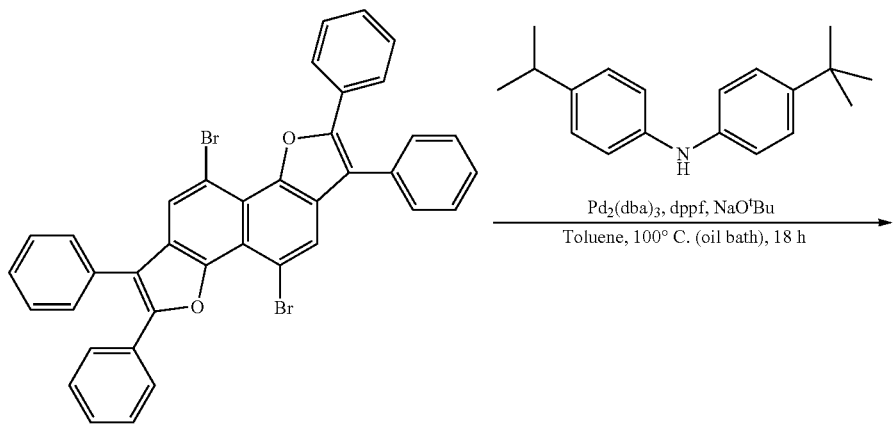

Intermediate C

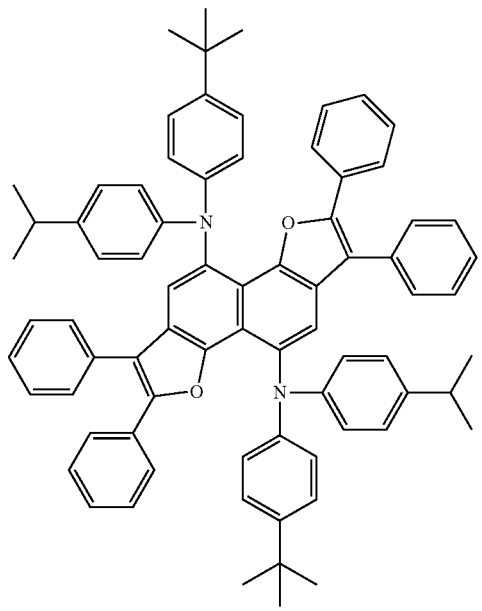

Compound 8

Catalyst amount of tris(dibenzylidene-acetone)-dipalladium(0) (Pd$_2$(dba)$_3$ (0.17 g, 0.19 mmole) and ligand 1.1'-Bis (diphenylphosphino)-ferrocene (dppf) (0.21 g, 0.38 mmole) were dissolved in toluene (50 mL) and purged with N$_2$. The mixture (dark brown) was stirred at RT for 10 min. Then dibromo Intermediate C (5.04 g, 7.5 mmole), 4-tert-butyl-phenyl-4'-isopropyl-phenyl amine (5.03 g, 20 mmole) and sodium tertbutyoxide (2.17 g, 20 mmole) dissolved in toluene (60 mL) and were added into the above catalyst mixture solution under N$_2$. The mixture was bubbled with N$_2$ for 15 min. (light brown solids), then heated at 115° C. (oil bath) for 18 h (dark brown solution). TLC checked no SM. The reaction mixture was poured into MeOH. The precipitate was filtered to give crude brown solid compound 8. It is highly blueish green fluorescence. The crude product was purified by running Florisil® (registered trademark of U.S. Silica Company) column, eluting with hex/CHCl$_3$ 1.5:1, 1:1 as eluents to give off-white solid. 6.6 g, yield: 85%, white solid. C$_{76}$H$_{70}$N$_2$: EI, MS m/z (%): 11042 (100, M$^+$).

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. An electroactive material having Formula I:

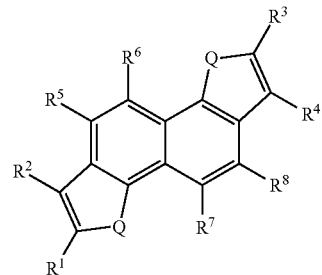

Formula I wherein:
Q is the same or different at each occurrence and is independently selected from the group consisting of BR, PR, PO, PO$_2$, and SiR$_2$;
R is the same or different at each occurrence and is independently selected from the group consisting of hydrogen, alkyl, aryl, alkenyl, and alkynyl;
R$^1$ through R$^8$ are the same or different and are independently selected from the group consisting of hydrogen, alkyl, aryl, halogen, hydroxyl, aryloxy, alkoxy, alkenyl, alkynyl, amino, alkylthio, phosphino, silyl, —COR, —COOR, —PO$_3$R$_2$, —OPO$_3$R$_2$, and CN.

2. The electroactive material of claim 1, wherein at least one of R$^2$ and R$^4$ is selected from the group consisting of alkyl, aryl, and diarylamino.

3. The electroactive material of claim 1, wherein at least one of R$^1$ and R$^3$ are selected from the group consisting of alkyl, aryl, and diarylamino.

4. The electroactive material of claim 1, wherein at least one of R$^5$, R$^6$, R$^7$, and R$^8$ is selected from the group consisting of alkyl, aryl, and diarylamino.

5. An electroactive polymer having at least one monomeric unit selected from the group consisting of Formula II and Formula III, or an electroactive polymer having at least two monomeric units wherein the first unit is of Formula II and a second unit is of Formula III:

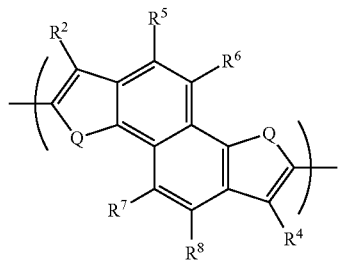

Formula II

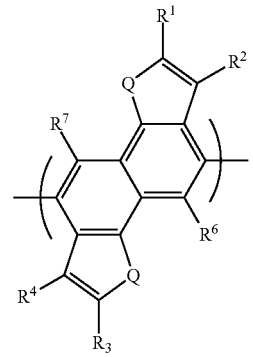

Formula III wherein:
- Q is the same or different at each occurrence and is independently selected from the group consisting of BR, PR, PO, PO$_2$, and SiR$_2$;
- R is the same or different at each occurrence and is independently selected from the group consisting of hydrogen, alkyl, aryl, alkenyl, and alkynyl; and
- R$^1$ through R$^8$ are the same or different and are independently selected from the group consisting of hydrogen, alkyl, aryl, halogen, hydroxyl, aryloxy, alkoxy, alkenyl, alkynyl, amino, alkylthio, phosphino, silyl, —COR, —COOR, —PO$_3$R$_2$, —OPO$_3$R$_2$, and CN.

6. The polymer of claim 5, wherein the polymer is a homopolymer.

7. The polymer of claim 5, having Formula IV or V:

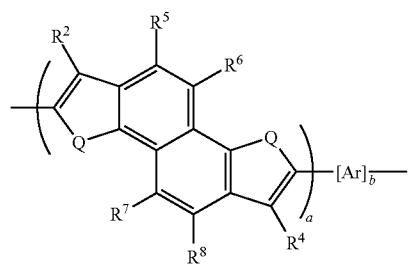

Formula IV

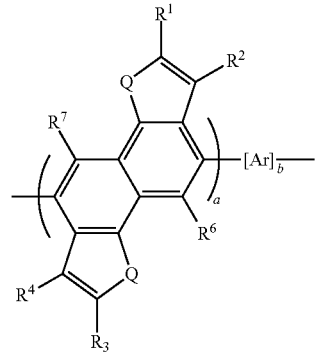

Formula V wherein:
- Ar is the same or different at each occurrence and is an aromatic unit;
- Q is the same or different at each occurrence and is independently selected from the group consisting of BR, PR, PO, PO$_2$, and SiR$_3$;
- R is the same or different at each occurrence and is independently selected from the group consisting of hydrogen, alkyl, aryl, alkenyl, and alkynyl;
- R$^1$ through R$^8$ are the same or different and are independently selected from the group consisting of hydrogen, alkyl, aryl, halogen, hydroxyl, aryloxy, alkoxy, alkenyl, alkynyl, amino, alkylthio, phosphino, silyl, —COR, —COOR, —PO$_3$R$_2$, —OPO$_3$R$_2$, and CN; and
- a and b represent mole fractions, such that a+b=1.

8. The polymer of claim 7, wherein Ar is selected from the group consisting of phenylene, naphthylene, biphenylene, binaphthylene, anthracenylene, fluorenylene, diarylamine and combinations thereof.

9. An organic electronic device comprising a first electrical contact, a second electrical contact and an electroactive layer therebetween, the electroactive layer comprising an electroactive material selected from the group consisting of a compound having Formula I, a polymer having at least one monomeric unit of Formula II, a polymer having at least one monomeric unit of Formula III, and a polymer having at least two monomeric units wherein the first unit if of Formula II and a second unit is of Formula III

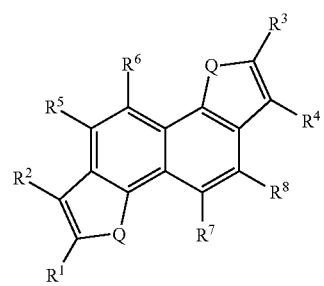

Formula I

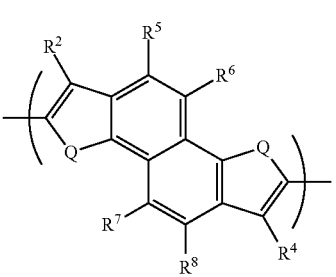

Formula II

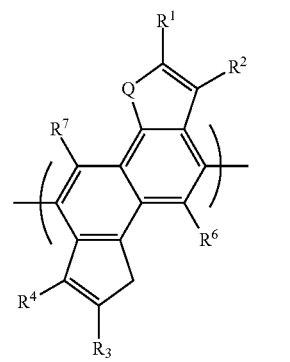

Formula III wherein:
- Q is the same or different at each occurrence and is independently selected from the group consisting of BR, PR, PO, PO$_2$, and SiR$_2$;
- R is the same or different at each occurrence and is independently selected from the group consisting of hydrogen, alkyl, aryl, alkenyl, and alkynyl;
- R$^1$ through R$^6$ are the same or different and are independently selected from the group consisting of hydrogen, alkyl, aryl, halogen, hydroxyl, aryloxy, alkoxy, alkenyl, alkynyl, amino, alkylthio, phosphino, silyl, —COR, —COOR, —PO$_3$R$_2$, —OPO$_3$R$_2$, and CN; and
- a and b represent mole fractions, such that a+b=1.

* * * * *